United States Patent
Lee

(10) Patent No.: US 11,187,704 B2
(45) Date of Patent: *Nov. 30, 2021

(54) IL-6 SIGNALING AND BREAST CANCER

(71) Applicant: City of Hope, Duarte, CA (US)

(72) Inventor: Peter P. Lee, Duarte, CA (US)

(73) Assignee: CITY OF HOPE, Duarte, CA (US)

( * ) Notice: Subject to any disclaimer, the term of this patent is extended or adjusted under 35 U.S.C. 154(b) by 85 days.

This patent is subject to a terminal disclaimer.

(21) Appl. No.: 16/660,524

(22) Filed: Oct. 22, 2019

(65) Prior Publication Data

US 2020/0116724 A1    Apr. 16, 2020

Related U.S. Application Data

(63) Continuation of application No. 15/806,883, filed on Nov. 8, 2017, now Pat. No. 10,481,159.

(60) Provisional application No. 62/419,813, filed on Nov. 9, 2016.

(51) Int. Cl.
  *G01N 33/574* (2006.01)
  *G01N 33/68* (2006.01)
  *C12Q 1/6886* (2018.01)

(52) U.S. Cl.
  CPC ..... *G01N 33/57415* (2013.01); *C12Q 1/6886* (2013.01); *G01N 33/6869* (2013.01); *C12Q 2600/118* (2013.01); *C12Q 2600/158* (2013.01); *G01N 2333/4703* (2013.01); *G01N 2333/5412* (2013.01); *G01N 2333/7155* (2013.01); *G01N 2800/54* (2013.01)

(58) Field of Classification Search
  None
  See application file for complete search history.

(56) References Cited

U.S. PATENT DOCUMENTS 10,481,159 B2    11/2019  Lee

OTHER PUBLICATIONS

Dethlefsen et al, Breast Cancer Res Treat; 2013; vol. 138, pp. 657-664.*
Shen et al, Tumor Biology, vol. 37, pp. 15359-15370, published on Sep. 22, 2016.*
Widschwendter, Clinical Cancer Research, 2002, vol. 8, pp. 3065-3074.*
Anderson, K.S. et al. (2010). Abstract 1906:IL-6-mediated activation of STAT3 inhibits APC and T cell function in metastatic breast cancer, *Proceedings AACR 101st Annual Meeting Apr. 17-21, 2010*, Washington D.C., 2 pages.
Bachelot, T. et al. (Jun. 2003). "Prognostic value of serum levels of interleukin 6 and of serum and plasma levels of vascular endothelial growth factor in hormone-refractory metastatic breast cancer patients," *Br J Cancer* 88(11):1721-1726.
Chang, Q. et al. (Jul. 2013). "The IL-6/JAK/Stat3 feed-forward loop drives tumorigenesis and metastasis," *Neoplasia* 15(7):848-862.
Dienz, O. et al. (Jan. 2009, e-published Oct. 8, 2008). "The effects of IL-6 on CD4 T cell responses," *Clin Immunol* 130(1):27-33.
Heo, T.H. et al. (Mar. 29, 2016). "Potential therapeutic implications of IL-6/IL-6R/gp130-targeting agents in breast cancer," *Oncotarget* 7(13):15460-15473.
Magi, B. et al. (2005). "Immunoblotting Techniques" in *Methods in Molecular Biology*, Third Edition, vol. 295, pp. 227-253.
Salgado, R. et al. (Feb. 20, 2003). "Circulating interleukin-6 predicts survival in patients with metastatic breast cancer.," *Int J Cancer* 103(5):642-646.

* cited by examiner

*Primary Examiner* — Elizabeth C. Kemmerer
*Assistant Examiner* — Fozia M Hamud
(74) *Attorney, Agent, or Firm* — Mintz, Levin, Cohn, Ferris, Glovsky and Popeo, P.C.

(57) ABSTRACT

The disclosure provides, inter alia, methods of detecting IL-6 signaling activity in T cells in breast cancer patients, such as breast cancer patients in remission.

12 Claims, 10 Drawing Sheets

Specification includes a Sequence Listing.

IL-6 SIGNALING AND BREAST CANCER

CROSS-REFERENCE TO RELATED APPLICATIONS

This application is a continuation of U.S. application Ser. No. 15/806,883 filed Nov. 8, 2017, issued as U.S. Pat. No. 10,481,159 which claims priority to U.S. Application No. 62/419,813 filed Nov. 9, 2016, the disclosure of which is incorporated by reference herein in its entirety.

STATEMENT AS TO RIGHTS TO INVENTIONS MADE UNDER FEDERALLY SPONSORED RESEARCH AND DEVELOPMENT

This invention was made with Government support under Grant Numbers W81XWH-10-1-0616 and W81XWH-06-1-0417 awarded by the U.S. Army Medical Research and Materiel Command and Grant Numbers AI07290-24 and CA130817, awarded by the National Institutes of Health. The Government has certain rights in the invention.

REFERENCE TO A "SEQUENCE LISTING," A TABLE, OR A COMPUTER PROGRAM LISTING APPENDIX SUBMITTED AS AN ASCII FIL

The Sequence Listing written in file 048440-631C01US Sequence Listing_ST25.TXT, created on Oct. 22, 2019, 1,458 bytes, machine format IBM-PC, MS-Windows operating system, is hereby incorporated by reference BACKGROUND Inflammation and adaptive immune responses play opposing roles in regulating tumor development, progression, and metastasis. Interleukin-6 (IL-6) is a pleiotropic cytokine with both pro- and anti-inflammatory properties and also acts directly on cancer cells to promote their survival and proliferation. Serum IL-6 levels are elevated and negatively associated with survival of cancer patients, which is generally attributed to the direct effects of IL-6 on cancer cells. There is a need in the art to further elucidate IL-6 modulation of the host immune response in cancer patients. The present disclosure addresses these and other needs in the art.

SUMMARY

The disclosure provides methods of detecting IL-6 activity in a breast cancer patient by obtaining a biological sample comprising T cells from the patient; contacting the biological sample with an IL-6 pathway detection agent capable of binding an IL-6 pathway protein, thereby forming a detectable complex; and detecting and/or quantifying the detectable complex, thereby detecting IL-6 activity in the breast cancer patient. In embodiments, the breast cancer patient is a breast cancer patient in remission, the biological sample is peripheral blood mononuclear cells, and the T cells are $CD4^+$ T cells.

The disclosure provides methods of detecting IL-6 activity in a breast cancer patient by obtaining a biological sample comprising T cells from the patient; contacting the biological sample with an IL-6 pathway probe capable of hybridizing an IL-6 pathway mRNA expression sequence, thereby forming a hybridization complex; and (iii) detecting and/or quantifying the hybridization complex, thereby detecting IL-6 activity in the breast cancer patient. In embodiments, the breast cancer patient is a breast cancer patient in remission, the biological sample is peripheral blood mononuclear cells, and the T cells are $CD4^+$ T cells.

The disclosure provides methods of detecting IL-6 activity in a breast cancer patient by obtaining a biological sample comprising T cells from the patient; isolating the T cells from the biological sample; culturing the T cells, thereby forming a T cell culture; and detecting one or more of the following in the T cell culture: Th17 cells, regulatory T cells (Treg), Th2 cells, Th1 cells, IL-17 levels, thereby detecting IL-6 activity in the breast cancer patient. In embodiments, the breast cancer patient is a breast cancer patient in remission, the biological sample is peripheral blood mononuclear cells, and the T cells are $CD4^+$ T cells.

The disclosure provides methods of treating an IL-6 pathway-defective patient, wherein the patient is a breast cancer remission patient, the method comprising administering a therapeutically effective amount of an anti-cancer agent to the patient. In embodiments, the IL-6 pathway defect is an impairment in the IL-6 signaling pathway in T cells, as described herein.

The disclosure provides methods of predicting relapse in a breast cancer patient in remission by obtaining a biological sample comprising T cells from the patient; contacting the biological sample with an IL-6 pathway detection agent capable of binding an IL-6 pathway protein, thereby forming a detectable complex; and detecting and/or quantifying the detectable complex, thereby detecting IL-6 activity in the breast cancer patient; wherein a different IL-6 activity relative to a standard control indicates an increased probability of breast cancer relapse in the breast cancer patient in remission. The standard control can be a healthy person or a breast cancer patient in remission who has not experienced relapse. In embodiments, the biological sample is peripheral blood mononuclear cells, and the T cells are $CD4^+$ T cells. In embodiments, the different IL-6 activity is a lower IL-6 activity.

The disclosure provides methods of predicting relapse in a breast cancer patient in remission by obtaining a biological sample comprising T cells from the patient; contacting the biological sample with an IL-6 pathway probe capable of hybridizing an IL-6 pathway mRNA expression sequence, thereby forming a hybridized complex; and detecting and/or quantifying the hybridized complex, thereby detecting IL-6 activity in the breast cancer patient; wherein a different IL-6 activity relative to a standard control indicates an increased probability of breast cancer relapse in the breast cancer patient in remission. The standard control can be a healthy person or a breast cancer patient in remission who has not experienced relapse. In embodiments, the biological sample is peripheral blood mononuclear cells, and the T cells are $CD4^+$ T cells. In embodiments, the different IL-6 activity is a lower IL-6 activity.

The disclosure provides solid supports comprising one or more IL-6 pathway detection agents capable of binding an IL-6 pathway protein or an IL-6 pathway mRNA expression sequence.

These and other embodiments of the disclosure are described in detail herein.

BRIEF DESCRIPTION OF THE DRAWINGS

FIG. 1A is a schematic representation of the experimental overview. Peripheral blood mononuclear cells (PBMCs) obtained from breast cancer patients and from healthy donors (H) were stimulated with IL-6 at 100 ng/ml for 15 mins. IL-6 induced phosphorylation of STAT1 and STAT3 (pSTATs) in naïve CD4+ T cells (CD3+ CD4+ CD45RA+) were determined by phosphoflow cytometry with anti-pSTAT1 (pY701) and anti-pSTAT3 (pY705) antibodies. IL-6 signaling responses are represented by AMFI (medium fluorescence intensity) which is the IL-6 stimulated MFI minus unstimulated MFI of pSTAT1 or pSTAT3. In FIG. 1B, IL-6 induced phosphorylation of STAT1 (p=0.003) in peripheral naïve CD4+ T cells were compared between breast cancer patients (n=57, median age 51, range 27-85) and age-matched healthy donors (n=26, median age 53, range 30-72). Unpaired t test. In FIG. 1C, IL-6 induced phosphorylation of STAT3 (p=0.0004) in peripheral naïve CD4+ T cells were compared between breast cancer patients (n=57, median age 51, range 27-85) and age-matched healthy donors (n=26, median age 53, range 30-72). Unpaired t test. In FIG. 1D, the association between IL-6 induced pSTAT1 and pSTAT3 in naïve CD4+ T cells from breast cancer patients was determined by Pearson's correlation coefficient test (r=0.79, p<0.0001).

In FIG. 2A, IL-6 plasma levels in healthy donors (mean 2.0 pg/ml, median 0.25 pg/ml) and breast cancer patients (mean 4.2 pg/ml, median 0 pg/ml) were determined by ELISA. Age-matched healthy donors (n=66, median age 58, range 18-72) were compared to breast cancer patients (n=70, median age 50, range 27-85). All breast cancer patient plasma was collected at diagnosis prior to surgery or any therapy. FIG. 2B shows IL-6 plasma level distributions (subdivided into 0-2 pg/ml, 2-10 pg/ml and >10 pg/ml) in the healthy donors and breast cancer patients. FIG. 2C shows that, among the healthy donors and breast cancer patients with normal IL-6 plasma levels (0-2 pg/ml), IL-6 induced phosphorylation of STAT1 (p=0.04) in peripheral naïve CD4+ T cells were compared. In FIG. 2D, among the healthy donors and breast cancer patients with normal IL-6 plasma levels (0-2 pg/ml), IL-6 induced phosphorylation of STAT3 (p=0.008) in peripheral naïve CD4+ T cells were compared. FIG. 2E shows the relationship between IL-6 plasma levels and IL-6 induced pSTAT1 in naïve CD4+ T cells from breast cancer patients, which was examined by Pearson's correlation coefficient test. ns=not significant. FIG. 2F shows the relationship between IL-6 plasma levels and IL-6 induced pSTAT3 in naïve CD4+ T cells from breast cancer patients, where were examined by Pearson's correlation coefficient test. ns=not significant.

In FIG. 3B, the associations between IL-6 induced pSTAT1 and the expression levels of gp130 plus IL-6Rα were determined by Pearson's correlation coefficient test (r=0.6, p=0.0005). In FIG. 3C, the associations between IL-6 induced pSTAT3 and the expression levels of gp130 plus IL-6Rα were determined by Pearson's correlation coefficient test (r=0.58, p=0.0009). In FIG. 3D, total RNA was extracted from isolated CD4+ naïve T cells and analyzed for the relative fold change by Q-PCR. mRNA levels of IL-6Rα (Il6r) (p=ns), gp130 (Il6st) (p=0.04) and ADAM17 (Adam17) (p=0.03) were compared between healthy donors (n=4) and breast cancer patients (n=4). In FIG. 3E, naïve CD4+ T cells were isolated from fresh PBMCs and were cultured in Th17 differentiation medium for 7 days. RORγt+ IL-17A+ cells identified Th17 cells by flow cytometry. The percentages of differentiated Th17 cells were compared between breast cancer patients (n=7) and age-matched healthy donors (n=8). (p=0.02). In FIG. 3F, supernatants were collected after 7 days of Th17 differentiation and the levels of IL-17 were determined by ELISA (pg/ml/1×10$^6$ cells). The levels of IL-17 were compared between breast cancer patients (n=7) and age-matched healthy donors (n=9). (p=0.04). In FIG. 3G, among the breast cancer patients (n=7), the associations between IL-6 induced pSTAT1 and level of IL-17 were determined by Pearson's correlation coefficient test. (r=0.9, p=0.001). All the blood from breast cancer patients were collected at diagnosis prior to surgery or any therapy. In FIG. 3H, among the breast cancer patients (n=7), the associations between IL-6 induced pSTAT3 and level of IL-17 were determined by Pearson's correlation coefficient test. (r=0.8, p=0.03). All the blood from breast cancer patients were collected at diagnosis prior to surgery or any therapy.

In FIG. 4A, IL-6 induced phosphorylation of STAT1 (p=0.0003) in peripheral naïve CD4+ T cells were compared between the non-relapsed and relapsed breast cancer patients, all of whom had been clinically followed for at least 36 months. All the blood from breast cancer patients were collected at diagnosis prior to surgery or any therapy. In FIG. 4B, IL-6 induced phosphorylation of STAT3 (p=0.0001) in peripheral naïve CD4+ T cells were compared between the non-relapsed and relapsed breast cancer patients, all of whom had been clinically followed for at least 36 months. All the blood from breast cancer patients were collected at diagnosis prior to surgery or any therapy. In FIG. 4C, Kaplan-Meier survival analysis was performed to compare relapse-free survival between breast cancer patients with lower and higher IL-6 signaling response (pSTAT1 p=0.004). The median IL-6 induced phosphorylation of STAT1 (ΔMFI) was used as the cut-off to divide breast cancer patients into lower and higher IL-6 signaling response groups. In FIG. 4D, Kaplan-Meier survival analysis was performed to compare relapse-free survival between breast cancer patients with lower and higher IL-6 signaling response (pSTAT3 p=0.005). The median IL-6 induced phosphorylation of STAT3 (ΔMFI) was used as the cut-off to divide breast cancer patients into lower and higher IL-6 signaling response groups.

DETAILED DESCRIPTION

Definitions

Figure 1A:
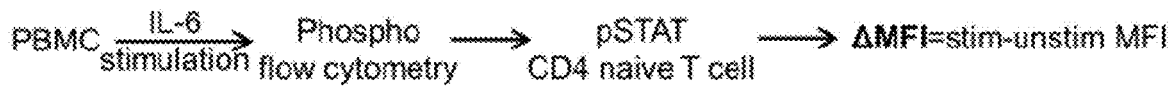
FIGS. 1A-1D show that IL-6 signaling response is impaired in peripheral naïve $CD4^+$ T cells from breast cancer patients. H=healthy donor. BC=breast cancer patient.

"Remission" means that the clinical signs and symptoms of breast cancer have been significantly diminished or have disappeared entirely based on clinical diagnostics, although cancerous cells can still exist in the body. Thus, it is contemplated that remission encompasses partial and complete remission. Remission can occur for any period of time, such as from one month to several years or more.

"Relapse" refers to the clinical diagnosis of a return of breast cancer after a period of remission.

"Relapse-free survival" or "RFS" refers to the time from the date of diagnosis of breast cancer to the date of relapse.

"Biological sample" refers to a material of biological origin (e.g., blood, plasma, cells, tissues, organs, fluids). In embodiments, "biological sample" is a blood sample.

"Peripheral blood" refers to blood circulating throughout the body. The components of peripheral blood include red blood cells (erythrocytes), white blood cells (leukocytes), and platelets.

"Peripheral blood mononuclear cell" or "PBMC" refers to cells in peripheral blood that have a nucleus, generally a round nucleus. Exemplary peripheral blood mononuclear cells include lymphocytes and monocytes. Exemplary lymphocytes are T cells, B cells, and NK cells. Peripheral blood mononuclear cells can be extracted from blood (e.g., peripheral blood) by methods known in the art.

"T cells" are a type of lymphocyte that originate in the hematopoietic stem cells in the bone marrow. Exemplary T cells include CD4$^+$ T cells, CD8 T$^+$ cells, memory T cells, regulatory T cells, natural killer T cells, mucosal associated invariant T cells, and gamma delta T cells. In embodiments, the T cells are CD4$^+$ T cells. In embodiments, the T cells are naïve CD4$^+$ T cells.

A "CD4+ T cell" or "CD4$^+$ T lymphocyte" as referred to herein is a lymphocyte that expresses the CD4 glycoprotein on its surface. CD4 T cells include helper T cells, which are T cells that help orchestrate the immune response, including antibody responses and killer T cell responses. CD4 T cell precursors differentiate into one of several subtypes, including TH1 (type 1 helper T cell), TH2 (type 2 helper T cell), TH3 (T helper 3 cells), TH17 (T helper 17 cells) or TFH (Follicular B helper T cells). These subtypes of helper T cells are characterized by their secretion of different cytokines to facilitate different types of immune responses.

"Naïve CD4+ T cell" is CD4+ T cell that has not yet been activated by an interaction with an antigen-MHC complex and has not yet differentiated into one of the subtypes.

"IL-6" refers to any of the recombinant or naturally-occurring forms of the Interleukin 6 (IL-6) or variants or homologs thereof that maintain IL-6 protein activity (e.g. within at least 50%, 80%, 90%, 95%, 96%, 97%, 98%, 99% or 100% activity compared to IL-6). In some aspects, the variants or homologs have at least 90%, 95%, 96%, 97%, 98%, 99% or 100% amino acid sequence identity across the whole sequence or a portion of the sequence (e.g. a 50, 100, 150 or 200 continuous amino acid portion) compared to a naturally occurring IL-6 polypeptide. In embodiments, IL-6 is the protein as identified by the UniProt reference P05231, homolog or functional fragment thereof.

"IL-6R" or "IL6R" refer to any of the recombinant or naturally-occurring forms of the Interleukin 6 receptor (IL-6R), also known as Cluster of Differentiation 126 (CD126), or variants or homologs thereof that maintain IL-6 receptor activity (e.g. within at least 50%, 80%, 90%, 95%, 96%, 97%, 98%, 99% or 100% activity compared to IL-6R). In some aspects, the variants or homologs have at least 90%, 95%, 96%, 97%, 98%, 99% or 100% amino acid sequence identity across the whole sequence or a portion of the sequence (e.g. a 50, 100, 150 or 200 continuous amino acid portion) compared to a naturally occurring IL-6 receptor. In embodiments, IL-6R is the protein as identified by the UniProt reference P08887, homolog or functional fragment thereof.

"Pathway" refers to a set of system components involved in two or more sequential molecular interactions that result in the production of a product or activity. A pathway can produce a variety of products or activities that can include, for example, intermolecular interactions, changes in expression of a nucleic acid or polypeptide, the formation or dissociation of a complex between two or more molecules, accumulation or destruction of a metabolic product, activation or deactivation of an enzyme or binding activity. Thus, the term "pathway" includes a variety of pathway types, such as, for example, a biochemical pathway, a gene expression pathway, and a regulatory pathway. Similarly, a pathway can include a combination of these exemplary pathway types.

"IL-6 pathway" or "IL-6 signaling pathway" refers to the intracellular signaling pathway activated when the cytokine IL-6 binds to the IL-6 receptor (IL-6R). The resulting complex then typically associates with gp130, inducing dimerization and the initiation of signaling through signal transducer and activator of transcription-3 (STAT3). The IL-6R is typically composed of two different subunits: (1) an alpha subunit that produces ligand specificity, and (2) g 130 that is a receptor subunit shared in common with other cytokines in the IL-6 family. Binding of IL-6 to its receptor initiates cellular events including activation of JAK kinases, e.g., JAK2, activation of ras-mediated signaling, and activation of PI3K- and Akt-mediated signaling. Activated JAK kinases phosphorylate and activate STAT transcription factors, i.e., JAK2 activates STAT3, that then move into the nucleus to activate transcription of genes containing STAT3 response elements, e.g., SOCS3. The ras-mediated pathway, acting through She, Grb-2 and Sos-1 upstream and activating Map kinases downstream, activates transcription factors such as EL-1 and NF-IL-6 (C/EBP-beta) that can act through their own cognate response elements in the genome. These factors and other transcription factors like AP-1 and SRF (serum response factor) that respond to many different signaling pathways come together to regulate a variety of complex promoters and enhancers that respond to IL-6 and other signaling factors. The IL-6 pathway includes, but is not limited to, the genes, mRNA expression sequences, and proteins.

"IL-6 pathway gene" refers to a gene in the IL-6 pathway. Such genes include STAT3, SOCS3, IFITM2, CEBPD, JUNB, TUBB2A, IL-6ST, CASP4, PROS1, TNFRSF1A, PVRL2, PHF21A, BCL3, NRP1, GLRX, and TGM2, which correspond to the following accession numbers: NM_213662, NM_003955, NM_006435, NM_005195, NM_002229, M 001069, NM_002184, NM_001225, NM_000313, NM_0.001065, NM_002856, NM_016621, NM_005178, NM_003873, NM_002064, and NM_004613, respectively, including homologs thereof.

"IL-6 pathway mRNA expression sequence" refers to an mRNA expression sequence in the IL-6 pathway. The IL-6 pathway mRNA expression sequence is an mRNA expression sequence transcribed by an IL-6 pathway gene. In embodiments, the IL-6 pathway mRNA expression sequence is STAT, phosphorylated STAT, gp130, ADAM 17, IL-6Rα, Jak, SOCS3, E3 ubiquitin ligase, protein tyrosine phosphatase, or E3 SUMO-protein ligase. In embodiments, the IL-6 pathway mRNA expression sequence is phosphorylated STAT, IL-6Rα, gp130, or ADAM 17. In embodiments, the IL-6 pathway mRNA expression sequence is STAT. In embodiments, the STAT is STAT1 or STAT3 In embodiments, the IL-6 pathway mRNA expression sequence is phosphorylated STAT. In embodiments, the phosphorylated STAT is phosphorylated STAT1 or phosphorylated STAT3.

"IL-6 pathway protein" refers to a protein in the IL-6 pathway. The IL-6 pathway protein can be any protein encoded by an IL-6 pathway gene. In embodiments, the IL-6 pathway protein is phosphorylated STAT, gp130, ADAM 17, IL-6Rα, Jak, SOCS3, E3 ubiquitin ligase, protein tyrosine phosphatase, or E3 SUMO-protein ligase. In embodiments, the IL-6 pathway protein is phosphorylated STAT, IL-6Rα, gp130, or ADAM 17. In embodiments, the IL-6 pathway protein is STAT. In embodiments, the STAT is STAT1 or STAT3. In embodiments, the IL-6 pathway protein is phosphorylated STAT. In embodiments, the phosphorylated STAT is phosphorylated STAT1 or phosphorylated STAT3.

"IL-6 activity" or "IL-6 signaling activity" refers to a cellular or biological event that occurs as a result of activation of the "IL-6 pathway" or "IL-6 signaling pathway." These cellular events include transcription (i.e., where the DNA of the IL-6 pathway gene is copied into an IL-6 pathway mRNA expression sequence) and translation (i.e., where the IL-6 pathway mRNA expression sequence encodes the IL-6 pathway protein).

"IL-6 pathway defective patient" refers to a patient who has a defect in their IL-6 pathway signaling. Methods for identifying an IL-6 pathway defective patient are described herein.

"IL-6 pathway detection agent" refers to a detection agent that can bind to an IL-6-pathway protein. The skilled artisan could readily select an appropriate detection agent based on the IL-6 pathway protein that should be detected, quantified, or both detected and quantified.

"IL-6 pathway probe" refers to a probe that can hybridize an IL-6-pathway mRNA expression sequence. The skilled artisan could readily select an appropriate probe based on the IL-6 pathway mRNA expression sequence that should be detected, quantified, or both detected and quantified.

"STAT1 protein" refers to any of the recombinant or naturally-occurring forms of the Signal transducer and activator of transcription 1 (STAT1) protein or variants or homologs thereof that maintain STAT1 protein activity (e.g. within at least 50%, 80%, 90%, 95%, 96%, 97%, 98%, 99% or 100% activity compared to STAT3). In some aspects, the variants or homologs have at least 90%, 95%, 96%, 97%, 98%, 99% or 100% amino acid sequence identity across the whole sequence or a portion of the sequence (e.g. a 50, 100, 150 or 200 continuous amino acid portion) compared to a naturally occurring STAT1 polypeptide. In embodiments, the STAT1 protein is substantially identical to the protein identified by the UniProt reference number P42224 or a variant or homolog having substantial identity thereto.

"STAT3 protein" refers to any of the recombinant or naturally-occurring forms of the Signal transducer and activator of transcription 3 (STAT3) protein or variants or homologs thereof that maintain STAT3 protein activity (e.g. within at least 50%, 80%, 90%, 95%, 96%, 97%, 98%, 99% or 100% activity compared to STAT3). In some aspects, the variants or homologs have at least 90%, 95%, 96%, 97%, 98%, 99% or 100% amino acid sequence identity across the whole sequence or a portion of the sequence (e.g. a 50, 100, 150 or 200 continuous amino acid portion) compared to a naturally occurring STAT3 polypeptide. In embodiments, the STAT3 protein is substantially identical to the protein identified by the UniProt reference number P40763 or a variant or homolog having substantial identity thereto.

"ADAM 17" or "ADAM 17 protease" refers to any of the recombinant or naturally-occurring forms of the disintegrin and metalloprotease domain-containing (ADAM) protein 17 or variants or homologs thereof that maintain ADAM 17 activity (e.g. within at least 50%, 80%, 90%, 95%, 96%, 97%, 98%, 99% or 100% activity compared to ADAM 17). In some aspects, the variants or homologs have at least 90%, 95%, 96%, 97%, 98%, 99% or 100% amino acid sequence identity across the whole sequence or a portion of the sequence (e.g. a 50, 100, 150 or 200 continuous amino acid portion) compared to a naturally occurring ADAM 17 polypeptide. In embodiments, ADAM 17 is the protein as identified by the NCBI sequence reference GI:73747889, homolog or functional fragment thereof.

"Detection agent" refers to (i) a compound that is capable of binding (covalently or non-covalently) a protein and (ii) a detectable label. The "detection agent" can be an "indirect detection agent" or a "direct detection agent." An "indirect detection agent" refers to a compound that is capable of binding (covalently or non-covalently) a protein that cannot be detected itself, but is detected using a separate, distinct detectable label that specifically binds (covalently or non-covalently) to the compound that is capable of binding the protein. A "direct detection agent" refers to a compound that is capable of binding (covalently or non-covalently) a protein and is also a detectable label (e.g., whether the compound and detectable label are the same compound or whether the compound and detectable label are separate, bound compounds). Exemplary detection agents that can interact with a protein include antibodies (monoclonal or polyclonal), RNA, DNA, biotin, and the like. In one embodiment, the detection agent that interacts with the protein is, or includes, an antibody. In embodiments, the detection agent comprises an antibody bound to an enzyme. In embodiments, the detection agent includes a primary antibody bound to a secondary antibody that is bound to an enzyme. In embodiments, the detection agent comprises biotin and streptavidin. In embodiments, the detection agent comprises biotin, streptavidin, and an enzyme. In embodiments, the detection agent comprises biotin and avidin. In embodiments, the detection agent comprises biotin, avidin, and an enzyme. "Protein" refers to an IL-6 pathway protein.

"Detectable label" refers to a moiety that indicates the presence of a corresponding molecule to which it is bound. A "detectable label" can be an indirect or direct label. An "indirect label" refers to a moiety, or ligand, that is detected using a labeled secondary agent, or ligand-binding partner, that specifically binds to the indirect label. A "direct label" refers to a moiety that is detectable in the absence of a ligand-binding partner interaction. Exemplary detectable labels include fluorescent labels (including, e.g., quenchers or absorbers), non-fluorescent labels, colorimetric labels, chemiluminescent labels, bioluminescent labels, radioactive labels (such as $^3$H, $^{35}$S, $^{32}$P, $^{125}$I, $^{57}$CO or $^{14}$C), mass-modifying groups, antibodies, antigens, biotin, haptens, digoxigenin, enzymes (including, e.g., peroxidase, phosphatase, etc.), and the like.

"Detectable complex" refers to a composition comprising (i) a detection agent and (ii) a protein, where the detection agent and protein are bound (covalently or non-covalently) together, and where the detectable complex can be identified and/or quantified by methods known in the art. "Protein" refers to an IL-6 pathway protein.

"Probe" refers to a nucleotide that includes a target-binding region that is substantially complementary to a target sequence in a target nucleic acid (e.g., IL-6 pathway mRNA expression sequence) and, thus, is capable of forming a hydrogen-bonded duplex with the target nucleic acid. Typically, the probe is a single-stranded probe, having one or more detectable labels to permit the detection of the probe following hybridization to its complementary target.

"Hybridization complex" refers to a composition containing (i) a probe and (ii) a target nucleic acid, where the probe and target nucleic acid are bound (e.g., hybridized) together, and where the hybridization complex can be identified and/or quantified by methods known in the art. The "target nucleic acid" refers to an IL-6 pathway mRNA expression sequence.

"Complementary" refers to sequence complementarity between two different nucleic acid strands or between two regions of the same nucleic acid strand. A first region of a nucleic acid is complementary to a second region of the same or a different nucleic acid if, when the two regions are arranged in an anti-parallel fashion, at least one nucleotide residue of the first region is capable of base pairing (i.e., hydrogen bonding) with a residue of the second region, thus forming a hydrogen-bonded duplex.

"Substantially complementary" refers to two nucleic acid strands (e.g., a strand of a target nucleic acid and a complementary single-stranded oligonucleotide probe) that are capable of base pairing with one another to form a stable hydrogen-bonded duplex under stringent hybridization conditions, including the isothermal hybridization conditions described herein. In general, "substantially complementary" refers to two nucleic acids having at least 75%, for example, about 80%, 85%, 90%, 95%, 97%, 98%, 99% or 100% complementarity. The term "stringent" refers to hybridization conditions that affect the stability of hybrids, e.g., temperature, salt concentration, pH, formamide concentration, and the like. These conditions are empirically optimized to maximize specific binding, and minimize nonspecific binding, of a probe to a target nucleic acid (e.g., RNA).

Hybridization assays are well known in the art, and include, for example, sandwich hybridization assays, competitive hybridization assays, hybridization-ligation assays, dual ligation hybridization assays, nuclease hybridization assays, and the like. Nucleic acids "hybridize" when they associate, typically in solution. Nucleic acids hybridize due to a variety of well-characterized physicochemical forces, such as hydrogen bonding, solvent exclusion, base stacking and the like. In certain embodiments, hybridization occurs under conventional hybridization conditions, such as under stringent conditions as described, for example, in Sambrook et al., in "Molecular Cloning: A Laboratory Manual" (1989), Eds. J. Sambrook, E. F. Fritsch and T. Maniatis, Cold Spring Harbour Laboratory Press, Cold Spring Harbour, N.Y., which is incorporated by reference. Such conditions are, for example, hybridization in 6×SSC, pH 7.0/0.1% SDS at about 45° C. for 18-23 hours, followed by a washing step with 2×SSC/1% SDS at 50° C. In order to select the stringency, the salt concentration in the washing step can, for example, be chosen between 2×SSC/0.1% SDS at room temperature for low stringency and 0.2×SSC/0.1% SDS at 50° C. for high stringency. In addition, the temperature of the washing step can be varied between room temperature (ca. 22° C.), for low stringency, and 65° C. to 70° C. for high stringency. Also contemplated are polynucleotides that hybridize at lower stringency hybridization conditions. Changes in the stringency of hybridization and signal detection are primarily accomplished through the manipulation of, e.g., formamide concentration (lower percentages of formamide result in lowered stringency), salt conditions, or temperature. For example, lower stringency conditions include an overnight incubation at 37° C. in a solution comprising 6×SSPE (20×SSPE=3M NaCl; 0.2M $NaH_2PO_4$; 0.02M EDTA, pH 7.4), 0.5% SDS, 30% formamide, 100 mg/mL salmon sperm blocking DNA, followed by washes at 50° C. with 1×SSPE, 0.1% SDS. In addition, to achieve even lower stringency, washes performed following stringent hybridization can be done at higher salt concentrations (e.g., 5×SSC). Variations in the above conditions may be accomplished through the inclusion and/or substitution of alternate blocking reagents used to suppress background in hybridization experiments. The inclusion of specific blocking reagents may require modification of the hybridization conditions described herein, due to problems with compatibility. An extensive guide to the hybridization of nucleic acids is found in Tij ssen (1993) Laboratory Techniques in Biochemistry and Molecular Biology—Hybridization with Nucleic Acid Probes part I chapter 2, "Overview of principles of hybridization and the strategy of nucleic acid probe assays," (Elsevier, New York), as well as in Ausubel (Ed.) Current Protocols in Molecular Biology, Volumes I, II, and III, (1997), which are each incorporated by reference. Hames and Higgins (1995) Gene Probes 1 IRL Press at Oxford University Press, Oxford, England, (Hames and Higgins 1) and Hames and Higgins (1995) Gene Probes 2 IRL Press at Oxford University Press, Oxford, England (Hames and Higgins 2) provide details on the synthesis; labeling, detection and quantification of DNA and RNA, including oligonucleotides. Both Hames and Higgins 1 and 2 are incorporated by reference.

"Nucleic acid" refers to a polymer having multiple nucleotide monomers. "Nucleic acid" includes IL-6 pathway mRNA expression sequence. A nucleic acid can be single- or double-stranded, and can be DNA (e.g., cDNA or genomic DNA), RNA, or hybrid polymers (e.g., DNA/RNA). Nucleic acids can be chemically or biochemically modified and/or can contain non-natural or derivatized nucleotide bases. Nucleic acid modifications include, for example, methylation, substitution of one or more of the naturally occurring nucleotides with an analog, internucleotide modifications such as uncharged linkages (e.g., methyl phosphonates, phosphotriesters, phosphoamidates, carbamates, and the like), charged linkages (e.g., phosphorothioates, phosphorodithioates, and the like), pendent moieties (e.g., polypeptides), intercalators (e.g., acridine, psoralen, and the like), chelators, alkylators, and modified linkages (e.g., alpha anomeric nucleic acids, and the like). Nucleic acids also include synthetic molecules that mimic nucleic acids in their ability to bind to a designated sequence via hydrogen bonding and other chemical interactions. Typically, the nucleotide monomers are linked via phosphodiester bonds, although synthetic forms of nucleic acids can comprise other linkages (e.g., peptide nucleic acids (also referred to herein as "PNAs. Nucleic acids can also include, for example, conformationally restricted nucleic acids (e.g., "locked nucleic acids" or "LNAs."

"DNA" and "RNA" refer to deoxyribonucleic acid and ribonucleic acid, respectively.

Where a method disclosed herein refers to "amplifying" a nucleic acid, the term "amplifying" refers to a process in which the nucleic acid is exposed to at least one round of extension, replication, or transcription in order to increase (e.g., exponentially increase) the number of copies (including complimentary copies) of the nucleic acid. The process can be iterative including multiple rounds of extension, replication, or transcription. Various nucleic acid amplification techniques are known in the art, such as PCR amplification or rolling circle amplification.

A "primer" as used herein refers to a nucleic acid that is capable of hybridizing to a complimentary nucleic acid sequence in order to facilitate enzymatic extension, replication or transcription.

The terms "identical" or percent "identity," in the context of two or more nucleic acids, refer to two or more sequences or subsequences that are the same or have a specified percentage of nucleotides that are the same (i.e., about 60% identity, preferably 65%, 70%, 75%, 80%, 85%, 90%, 91%, 92%, 93%, 94%, 95%, 96%, 97%, 98%, 99%, or higher identity over a specified region, when compared and aligned for maximum correspondence over a comparison window or designated region) as measured using a BLAST or BLAST 2.0 sequence comparison algorithms with default parameters described below, or by manual alignment and visual inspection. See e.g., the NCBI web site at ncbi.nlm.nih.gov/BLAST. Such sequences are then said to be "substantially identical." This definition also refers to, or may be applied to, the compliment of a test sequence. The definition also includes sequences that have deletions and/or additions, as well as those that have substitutions. As described below, the preferred algorithms can account for gaps and the like. Preferably, identity exists over a region that is at least about 25 amino acids or nucleotides in length, or more preferably over a region that is 50-100 amino acids or nucleotides in length.

A variety of methods of specific DNA and RNA measurements that use nucleic acid hybridization techniques are known to those of skill in the art (see, Sambrook, Id.). Some methods involve electrophoretic separation (e.g., Southern blot for detecting DNA, and Northern blot for detecting RNA), but measurement of DNA and RNA can also be carried out in the absence of electrophoretic separation (e.g., quantitative PCR, dot blot, or array).

The sensitivity of the hybridization assays may be enhanced through use of a nucleic acid amplification system that multiplies the target nucleic acid being detected. Amplification can also be used for direct detection techniques. Examples of such systems include the polymerase chain reaction (PCR) system and the ligase chain reaction (LCR) system. Other methods include the nucleic acid sequence based amplification (NASBA, Cangene, Mississauga, Ontario) and Q Beta Replicase systems. These systems can be used to directly identify mutants where the PCR or LCR primers are designed to be extended or ligated only when a selected sequence is present. Alternatively, the selected sequences can be generally amplified using, for example, nonspecific PCR primers and the amplified target region later probed for a specific sequence indicative of a mutation. It is understood that various detection probes, including TAQMAN® and molecular beacon probes can be used to monitor amplification reaction products in real time.

"Contact" or "contacting" is used in accordance with its plain ordinary meaning and refers to the process of allowing at least two distinct species (e.g. chemical compounds including biomolecules, or cells) to become sufficiently proximal to react, interact or physically touch. It should be appreciated, however, that the resulting reaction product can be produced directly from a reaction between the added reagents or from an intermediate from one or more of the added reagents which can be produced in the reaction mixture. The term "contacting" may include allowing two species to react, interact, or physically touch, wherein the two species may be a compound as described herein and a protein or enzyme. In embodiments, contacting includes allowing a detection agent to interact with an IL-6 pathway protein, thereby forming a detectable complex. In embodiments, contacting includes allowing a probe to interact with an IL-6 pathway mRNA expression sequence, thereby forming a hybridization complex.

"Solid support" refers to a physical structure which can bind detection agents, probes, analytes, and/or reagents, covalently or non-covalently, in a device or method disclosed herein and embodiments thereof. Use of solid supports can facilitate detection and/or separation of analytes, e.g., splice isoforms, proteins coded by splice isoforms, RNA, nucleic acids, and the like. The choice of solid support for use in the present devices and methods is based upon the desired assay format and performance characteristics. Acceptable solid supports for use in the present devices and methods can vary widely. A solid support can be porous or nonporous. It can be continuous or non-continuous, and flexible or nonflexible. A solid support can be made of a variety of materials including ceramic, glass, silicon, metal, organic polymeric materials, or combinations thereof. In embodiments, the solid support is a resin or a bead. In embodiments, an antibody can be immobilized on a solid support, e.g., magnetic or chromatographic matrix particles, the surface of an assay plate (e.g., microtiter wells), pieces of a solid substrate material or membrane (e.g., plastic, nylon, paper), and the like. In embodiments, the solid support is a micro-titer plate. In embodiments, the microtiter plate is a polystyrene micro-titer plate. In embodiments, the solid support can be a microchip upon which nucleic acid reagent is affixed. In embodiments, binding of a portion of an analyte (e.g., splice isoform sample) to a nucleic acid reagent affixed on a microchip results in formation of a detectable duplex nucleic acid. In embodiments, the solid support is a nitrocellulose or PVDF membrane. In embodiments, the solid support includes a protein binding surface which can be a microtiter plate, a colloidal metal particle, an iron oxide particle, a latex particle, a polymeric bead, and any combination thereof. In embodiments, antibodies or other polypeptides can be immobilized onto a solid support for use in assays. Solid phases that may be used to immobilize specific binding members include those developed and/or used as solid phases in solid phase binding assays. Examples of suitable solid phases include membrane filters, cellulose-based papers, beads (including polymeric, latex and paramagnetic particles), glass, silicon wafers, microparticles, nanoparticles, TENTAGEL®, AGROGEL®, PEGA® gels, SPOCC® gels, and multiple-well plates.

"Control" or "control experiment" or "standard control" is used in accordance with its plain ordinary meaning and refers to an experiment in which the subjects or reagents of the experiment are treated as in a parallel experiment except for omission of a procedure, reagent, or variable of the experiment. In some instances, the control is used as a standard of comparison in evaluating experimental effects. In embodiments, the control is patient population (e.g., patients who have never had breast cancer) who have been evaluated similarly to a second, different patient population (e.g., patients who have breast cancer, patients who are in remission from breast cancer). In embodiments, the control is the condition or data obtained from healthy patients. In embodiments, the control is the condition or data obtained from breast cancer patients who are in remission and who have not relapsed.

"Treating" or "treatment" refers to any indicia of success in the treatment or amelioration of cancer, particularly breast cancer, including any obj ective or subj ective parameter such as abatement; remission; diminishing of symptoms or making the condition more tolerable to the patient; slowing in the rate of degeneration or decline; making the final point of degeneration less debilitating; improving a patient's physical or mental well-being. The treatment or amelioration of symptoms can be based on objective or subjective parameters. For example, certain methods herein treat breast cancer. For example certain methods herein treat breast cancer by decreasing a symptom of breast cancer. Symptoms of breast cancer would be known or may be determined by a person of ordinary skill in the art. Breast cancer can be treated with any effective anti-cancer therapy known in the art, such as hormone replacement therapy, chemotherapeutic agents, radiation therapy, surgery, or a combination of two or more thereof.

"Patient" or "subject" in need thereof refers to a living organism suffering from or prone to a disease or condition that can be treated by administration of a pharmaceutical composition as provided herein. In some embodiments, a patient is human. In embodiments, the patient is a human with breast cancer. In embodiments, the patient is a woman with breast cancer. In embodiments, the patient is a man with breast cancer. In embodiments, the patient is a human with breast cancer in remission. In embodiments, the patient is a woman with breast cancer in remission.

"Breast cancer patient" or "breast cancer subject" refers to a patient or subject with breast cancer.

"Breast cancer" refers to a malignant tumor that develops from cells in the breast. Usually breast cancer begin: (i) in the cells of the lobules, which are the milk-producing glands; (ii) in the cells of the ducts, the passages that drain milk from the lobules to the nipple; or (iii) in the stromal tissues, which include the fatty and fibrous connective tissues of the breast. Types of breast cancer include ductal carcinoma in situ, invasive ductal carcinoma, tubular carcinoma of the breast, medullary carcinoma of the breast, mucinous carcinoma of the breast, papillary carcinoma of the breast, cribriform carcinoma of the breast, invasive lobular carcinoma, inflammatory breast cancer, lobular carcinoma in situ, and the like. The breast cancer may also be of a molecular sub-type, such as luminal A, luminal B, triple negative, HER2, and normal-like. The breast cancer can be primary breast cancer or metastatic breast cancer. The breast cancer can be any stage, including Stage 0, IA, IB, IIA, IIB, IIIA, IIIB, IIIC, or IV.

"Modulation", "modulate", or "modulator" are used in accordance with their plain ordinary meaning and refer to the act of changing or varying one or more properties. "Modulator" refers to a composition that increases or decreases the level of a target molecule or the function of a target molecule or the physical state of the target of the molecule. "Modulation" refers to the process of changing or varying one or more properties. For example, as applied to the effects of a modulator on a biological target, to modulate means to change by increasing or decreasing a property or function of the biological target or the amount of the biological target.

"Anti-cancer agent" or "anti-cancer drug" is used in accordance with its plain ordinary meaning and refers to hormone replacement therapy, radiation therapy, or a composition (e.g. compound, drug, antagonist, inhibitor, modulator) having antineoplastic properties or the ability to inhibit the growth or proliferation of cells. In some embodiments, an anti-cancer agent is hormone replacement therapy. In some embodiments, an anti-cancer agent is radiation therapy. In some embodiments, an anti-cancer agent is a chemotherapeutic.

Examples of anti-cancer agents include, but are not limited to, anti-androgens (e.g., Casodex, Flutamide, MDV3100, or ARN-509), MEK (e.g. MEK1, MEK2, or MEK1 and MEK2) inhibitors (e.g. XL518, CI-1040, PD035901, selumetinib/AZD6244, GSK 120212/trametinib, GDC-0973, ARRY-162, ARRY-300, AZD8330, PD0325901, U0126, PD98059, TAK-733, PD318088, AS703026, BAY 869766), alkylating agents (e.g., cyclophosphamide, ifosfamide, chlorambucil, busulfan, melphalan, mechlorethamine, uramustine, thiotepa, nitrosoureas, nitrogen mustards (e.g., mechloroethamine, cyclophosphamide, chlorambucil, meiphalan), ethylenimine and methylmelamines (e.g., hexamethylmelamine, thiotepa), alkyl sulfonates (e.g., busulfan), nitrosoureas (e.g., carmustine, lomusitne, semustine, streptozocin), triazenes (decarbazine)), anti-metabolites (e.g., 5-azathioprine, leucovorin, capecitabine, fludarabine, gemcitabine, pemetrexed, raltitrexed, folic acid analog (e.g., methotrexate), or pyrimidine analogs (e.g., fluorouracil, floxouridine, Cytarabine), purine analogs (e.g., mercaptopurine, thioguanine, pentostatin), etc.), plant alkaloids (e.g., vincristine, vinblastine, vinorelbine, vindesine, podophyllotoxin, paclitaxel, docetaxel, etc.), topoisomerase inhibitors (e.g., irinotecan, topotecan, amsacrine, etoposide (VP16), etoposide phosphate, teniposide, etc.), antitumor antibiotics (e.g., doxorubicin, adriamycin, daunorubicin, epirubicin, actinomycin, bleomycin, mitomycin, mitoxantrone, plicamycin, etc.), platinum-based compounds (e.g. cisplatin, oxaloplatin, carboplatin), anthracenedione (e.g., mitoxantrone), substituted urea (e.g., hydroxyurea), methyl hydrazine derivative (e.g., procarbazine), adrenocortical suppressant (e.g., mitotane, aminoglutethimide), epipodophyllotoxins (e.g., etoposide), antibiotics (e.g., daunorubicin, doxorubicin, bleomycin), enzymes (e.g., L-asparaginase), inhibitors of mitogen-activated protein kinase signaling (e.g. U0126, PD98059, PD184352, PD0325901, ARRY-142886, SB239063, SP600125, BAY 43-9006, wortmannin, or LY294002, Syk inhibitors, mTOR inhibitors, antibodies (e.g., rituxan), gossyphol, genasense, polyphenol E, Chlorofusin, all trans-retinoic acid (ATRA), bryostatin, tumor necrosis factor-related apoptosis-inducing ligand (TRAIL), 5-aza-2'-deoxycytidine, all trans retinoic acid, doxorubicin, vincristine, etoposide, gemcitabine, imatinib (Gleevec®), geldanamycin, 17-N-Allylamino-17-Demethoxygeldanamycin (17-AAG), flavopiridol, LY294002, bortezomib, trastuzumab, BAY 11-7082, PKC412, PD184352, 20-epi-1, 25 dihydroxyvitamin D3; 5-ethynyluracil; abiraterone; aclarubicin; acylfulvene; adecypenol; adozelesin; aldesleukin; ALL-TK antagonists; altretamine; ambamustine; amidox; amifostine; aminolevulinic acid; amrubicin; amsacrine; anagrelide; anastrozole; andrographolide; angiogenesis inhibitors; antagonist D; antagonist G; antarelix; anti-dorsalizing morphogenetic protein-1; antiandrogen, prostatic carcinoma; antiestrogen; antineoplaston; antisense oligonucleotides; aphidicolin glycinate; apoptosis gene modulators; apoptosis regulators; apurinic acid; ara-CDP-DL-PTBA; arginine deaminase; asulacrine; atamestane; atrimustine; axinastatin 1; axinastatin 2; axinastatin 3; azasetron; azatoxin; azatyrosine; baccatin III derivatives; balanol; batimastat; BCR/ABL antagonists; benzochlorins; benzoylstaurosporine; beta lactam derivatives; beta-alethine; betaclamycin B; betulinic acid; bFGF inhibitor; bicalutamide; bisantrene; bisaziridinylspermine; bisnafide; bistratene A; bizelesin; breflate; bropirimine; budotitane; buthionine sulfoximine; calcipotriol; calphostin C; camptothecin derivatives; canarypox IL-2; capecitabine; carboxamide-amino-triazole; carboxyamidotriazole; CaRest M3; CARN 700; cartilage derived inhibitor; carzelesin; casein kinase inhibitors (ICOS); castanospermine; cecropin B; cetrorelix; chlorins; chloroquinoxaline sulfonamide; cicaprost; cis-porphyrin; cladribine; clomifene analogues; clotrimazole; collismycin A; collismycin B; combretastatin A4; combretastatin analogue; conagenin; crambescidin 816; crisnatol; cryptophycin 8; cryptophycin A derivatives; curacin A; cyclopentanthraquinones; cycloplatam; cypemycin; cytarabine ocfosfate; cytolytic factor; cytostatin; dacliximab; decitabine; dehydrodidemnin B; deslorelin; dexamethasone; dexifosfamide; dexrazoxane; dexverapamil; diaziquone; didemnin B; didox; diethylnorspermine; dihydro-5-azacytidine; 9-dioxamycin; diphenyl spiromustine; docosanol; dolasetron; doxifluridine; droloxifene; dronabinol; duocarmycin SA; ebselen; ecomustine; edelfosine; edrecolomab; eflornithine; elemene; emitefur; epirubicin;

epristeride; estramustine analogue; estrogen agonists; estrogen antagonists; etanidazole; etoposide phosphate; exemestane; fadrozole; fazarabine; fenretinide; filgrastim; finasteride; flavopiridol; flezelastine; fluasterone; fludarabine; fluorodaunorunicin hydrochloride; forfenimex; formestane; fostriecin; fotemustine; gadolinium texaphyrin; gallium nitrate; galocitabine; ganirelix; gelatinase inhibitors; gemcitabine; glutathione inhibitors; hepsulfam; heregulin; hexamethylene bisacetamide; hypericin; ibandronic acid; idarubicin; idoxifene; idramantone; ilmofosine; ilomastat; imidazoacridones; imiquimod; immunostimulant peptides; insulin-like growth factor-1 receptor inhibitor; interferon agonists; interferons; interleukins; iobenguane; iododoxorubicin; ipomeanol, 4-; iroplact; irsogladine; isobengazole; isohomohalicondrin B; itasetron; jasplakinolide; kahalalide F; lamellarin-N triacetate; lanreotide; leinamycin; lenograstim; lentinan sulfate; leptolstatin; letrozole; leukemia inhibiting factor; leukocyte alpha interferon; leuprolide+estrogen+progesterone; leuprorelin; levamisole; liarozole; linear polyamine analogue; lipophilic disaccharide peptide; lipophilic platinum compounds; lissoclinamide 7; lobaplatin; lombricine; lometrexol; lonidamine; losoxantrone; lovastatin; loxoribine; lurtotecan; lutetium texaphyrin; lysofylline; lytic peptides; maitansine; mannostatin A; marimastat; masoprocol; maspin; matrilysin inhibitors; matrix metalloproteinase inhibitors; menogaril; merbarone; meterelin; methioninase; metoclopramide; MIF inhibitor; mifepristone; miltefosine; mirimostim; mismatched double stranded RNA; mitoguazone; mitolactol; mitomycin analogues; mitonafide; mitotoxin fibroblast growth factor-saporin; mitoxantrone; mofarotene; molgramostim; monoclonal antibody, human chorionic gonadotrophin; monophosphoryl lipid A+myobacterium cell wall sk; mopidamol; multiple drug resistance gene inhibitor; multiple tumor suppressor 1-based therapy; mustard anticancer agent; mycaperoxide B; mycobacterial cell wall extract; myriaporone; N-acetyldinaline; N-substituted benzamides; nafarelin; nagrestip; naloxone+pentazocine; napavin; naphterpin; nartograstim; nedaplatin; nemorubicin; neridronic acid; neutral endopeptidase; nilutamide; nisamycin; nitric oxide modulators; nitroxide antioxidant; nitrullyn; O6-benzylguanine; octreotide; okicenone; oligonucleotides; onapristone; ondansetron; ondansetron; oracin; oral cytokine inducer; ormaplatin; osaterone; oxaliplatin; oxaunomycin; palauamine; palmitoylrhizoxin; pamidronic acid; panaxytriol; panomifene; parabactin; pazelliptine; pegaspargase; peldesine; pentosan polysulfate sodium; pentostatin; pentrozole; perflubron; perfosfamide; perillyl alcohol; phenazinomycin; phenylacetate; phosphatase inhibitors; picibanil; pilocarpine hydrochloride; pirarubicin; piritrexim; placetin A; placetin B; plasminogen activator inhibitor; platinum complex; platinum compounds; platinum-triamine complex; porfimer sodium; porfiromycin; prednisone; propyl bis-acridone; prostaglandin J2; proteasome inhibitors; protein A-based immune modulator; protein kinase C inhibitor; protein kinase C inhibitors, microalgal; protein tyrosine phosphatase inhibitors; purine nucleoside phosphorylase inhibitors; purpurins; pyrazoloacridine; pyridoxylated hemoglobin polyoxyethylerie conjugate; raf antagonists; raltitrexed; ramosetron; ras farnesyl protein transferase inhibitors; ras inhibitors; ras-GAP inhibitor; retelliptine demethylated; rhenium Re 186 etidronate; rhizoxin; ribozymes; RII retinamide; rogletimide; rohitukine; romurtide; roquinimex; rubiginone B 1; ruboxyl; safingol; saintopin; SarCNU; sarcophytol A; sargramostim; Sdi 1 mimetics; semustine; senescence derived inhibitor 1; sense oligonucleotides; signal transduction inhibitors; signal transduction modulators; single chain antigen-binding protein; sizofuran; sobuzoxane; sodium borocaptate; sodium phenylacetate; solverol; somatomedin binding protein; sonermin; sparfosic acid; spicamycin D; spiromustine; splenopentin; spongistatin 1; squalamine; stem cell inhibitor; stem-cell division inhibitors; stipiamide; stromelysin inhibitors; sulfinosine; superactive vasoactive intestinal peptide antagonist; suradista; suramin; swainsonine; synthetic glycosaminoglycans; tallimustine; tamoxifen methiodide; tauromustine; tazarotene; tecogalan sodium; tegafur; tellurapyrylium; telomerase inhibitors; temoporfin; temozolomide; teniposide; tetrachlorodecaoxide; tetrazomine; thaliblastine; thiocoraline; thrombopoietin; thrombopoietin mimetic; thymalfasin; thymopoietin receptor agonist; thymotrinan; thyroid stimulating hormone; tin ethyl etiopurpurin; tirapazamine; titanocene bichloride; topsentin; toremifene; totipotent stem cell factor; translation inhibitors; tretinoin; triacetyluridine; triciribine; trimetrexate; triptorelin; tropisetron; turosteride; tyrosine kinase inhibitors; tyrphostins; UBC inhibitors; ubenimex; urogenital sinus-derived growth inhibitory factor; urokinase receptor antagonists; vapreotide; variolin B; vector system, erythrocyte gene therapy; velaresol; veramine; verdins; verteporfin; vinorelbine; vinxaltine; vitaxin; vorozole; zanoterone; zeniplatin; zilascorb; zinostatin stimalamer, Adriamycin, Dactinomycin, Bleomycin, Vinblastine, Cisplatin, acivicin; aclarubicin; acodazole hydrochloride; acronine; adozelesin; aldesleukin; altretamine; ambomycin; ametantrone acetate; aminoglutethimide; amsacrine; anastrozole; anthramycin; asparaginase; asperlin; azacitidine; azetepa; azotomycin; batimastat; benzodepa; bicalutamide; bisantrene hydrochloride; bisnafide dimesylate; bizelesin; bleomycin sulfate; brequinar sodium; bropirimine; busulfan; cactinomycin; calusterone; caracemide; carbetimer; carboplatin; carmustine; carubicin hydrochloride; carzelesin; cedefingol; chlorambucil; cirolemycin; cladribine; crisnatol mesylate; cyclophosphamide; cytarabine; dacarbazine; daunorubicin hydrochloride; decitabine; dexormaplatin; dezaguanine; dezaguanine mesylate; diaziquone; doxorubicin; doxorubicin hydrochloride; droloxifene; droloxifene citrate; dromostanolone propionate; duazomycin; edatrexate; eflornithine hydrochloride; elsamitrucin; enloplatin; enpromate; epipropidine; epirubicin hydrochloride; erbulozole; esorubicin hydrochloride; estramustine; estramustine phosphate sodium; etanidazole; etoposide; etoposide phosphate; etoprine; fadrozole hydrochloride; fazarabine; fenretinide; floxuridine; fludarabine phosphate; fluorouracil; fluorocitabine; fosquidone; fostriecin sodium; gemcitabine; gemcitabine hydrochloride; hydroxyurea; idarubicin hydrochloride; ifosfamide; iimofosine; interleukin II (including recombinant interleukin II, or rIL.sub.2), interferon alfa-2a; interferon alfa-2b; interferon alfa-nl; interferon alfa-n3; interferon beta-1a; interferon gamma-1b; iproplatin; irinotecan hydrochloride; lanreotide acetate; letrozole; leuprolide acetate; liarozole hydrochloride; lometrexol sodium; lomustine; losoxantrone hydrochloride; masoprocol; maytansine; mechlorethamine hydrochloride; megestrol acetate; melengestrol acetate; melphalan; menogaril; mercaptopurine; methotrexate; methotrexate sodium; metoprine; meturedepa; mitindomide; mitocarcin; mitocromin; mitogillin; mitomalcin; mitomycin; mitosper; mitotane; mitoxantrone hydrochloride; mycophenolic acid; nocodazoie; nogalamycin; ormaplatin; oxisuran; pegaspargase; peliomycin; pentamustine; peplomycin sulfate; perfosfamide; pipobroman; piposulfan; piroxantrone hydrochloride; plicamycin; plomestane; porfimer sodium; porfiromycin; prednimustine; procarbazine hydrochloride; puromycin; puromycin hydrochloride; pyrazofurin; riboprine; rogletimide; safingol; safingol hydrochloride; semustine; simtrazene; sparfosate sodium; sparsomycin; spirogermanium hydrochloride; spiromustine; spiroplatin; streptonigrin; streptozocin; sulofenur; talisomycin; tecogalan sodium; tegafur; teloxantrone hydrochloride; temoporfin; teniposide; teroxirone; testolactone; thiamiprine; thioguanine; thiotepa; tiazofurin; tirapazamine; toremifene citrate; trestolone acetate; triciribine phosphate; trimetrexate; trimetrexate glucuronate; triptorelin; tubulozole hydrochloride; uracil mustard; uredepa; vapreotide; verteporfin; vinblastine sulfate; vincristine sulfate; vindesine; vindesine sulfate; vinepidine sulfate; vinglycinate sulfate; vinleurosine sulfate; vinorelbine tartrate; vinrosidine sulfate; vinzolidine sulfate; vorozole; zeniplatin; zinostatin; zorubicin hydrochloride, agents that arrest cells in the G2-M phases and/or modulate the formation or stability of microtubules, (e.g. Taxol.™ (i.e. paclitaxel), Taxotere.™, compounds comprising the taxane skeleton, Erbulozole (i.e. R-55104), Dolastatin 10 (i.e. DLS-10 and NSC-376128), Mivobulin isethionate (i.e. as CI-980), Vincristine, NSC-639829, Discodermolide (i.e. as NVP-XX-A-296), ABT-751 (Abbott, i.e. E-7010), Altorhyrtins (e.g. Altorhyrtin A and Altorhyrtin C), Spongistatins (e.g. Spongistatin 1, Spongistatin 2, Spongistatin 3, Spongistatin 4, Spongistatin 5, Spongistatin 6, Spongistatin 7, Spongistatin 8, and Spongistatin 9), Cemadotin hydrochloride (i.e. LU-103793 and NSC-D-669356), Epothilones (e.g. Epothilone A, Epothilone B, Epothilone C (i.e. desoxyepothilone A or dEpoA), Epothilone D (i.e. KOS-862, dEpoB, and desoxyepothilone B), Epothilone E, Epothilone F, Epothilone B N-oxide, Epothilone A N-oxide, 16-aza-epothilone B, 21-aminoepothilone B (i.e. BMS-310705), 21-hydroxyepothilone D (i.e. Desoxyepothilone F and dEpoF), 26-fluoroepothilone, Auristatin PE (i.e. NSC-654663), Soblidotin (i.e. TZT-1027), LS-4559-P (Pharmacia, i.e. LS-4577), LS-4578 (Pharmacia, i.e. LS-477-P), LS-4477 (Pharmacia), LS-4559 (Pharmacia), RPR-112378 (Aventis), Vincristine sulfate, DZ-3358 (Daiichi), FR-182877 (Fujisawa, i.e. WS-9885B), GS-164 (Takeda), GS-198 (Takeda), KAR-2 (Hungarian Academy of Sciences), BSF-223651 (BASF, i.e. ILX-651 and LU-223651), SAH-49960 (Lilly/Novartis), SDZ-268970 (Lilly/Novartis), AM-97 (Armad/Kyowa Hakko), AM-132 (Armad), AM-138 (Armad/Kyowa Hakko), IDN-5005 (Indena), Cryptophycin 52 (i.e. LY-355703), AC-7739 (Ajinomoto, i.e. AVE-8063A and CS-39.HCl), AC-7700 (Ajinomoto, i.e. AVE-8062, AVE-8062A, CS-39-L-Ser.HCl, and RPR-258062A), Vitilevuamide, Tubulysin A, Canadensol, Centaureidin (i.e. NSC-106969), T-138067 (Tularik, i.e. T-67, TL-138067 and TI-138067), COBRA-1 (Parker Hughes Institute, i.e. DDE-261 and WHI-261), H10 (Kansas State University), H16 (Kansas State University), Oncocidin Al (i.e. BTO-956 and DIME), DDE-313 (Parker Hughes Institute), Fijianolide B, Laulimalide, SPA-2 (Parker Hughes Institute), SPA-1 (Parker Hughes Institute, i.e. SPIKET-P), 3-IAABU (Cytoskeleton/Mt. Sinai School of Medicine, i.e. MF-569), Narcosine (also known as NSC-5366), Nascapine, D-24851 (Asta Medica), A-105972 (Abbott), Hemiasterlin, 3-BAABU (Cytoskeleton/Mt. Sinai School of Medicine, i.e. MF-191), TMPN (Arizona State University), Vanadocene acetylacetonate, T-138026 (Tularik), Monsatrol, Inanocine (i.e. NSC-698666), 3-IAABE (Cytoskeleton/Mt. Sinai School of Medicine), A-204197 (Abbott), T-607 (Tuiarik, i.e. T-900607), RPR-115781 (Aventis), Eleutherobins (such as Desmethyl eleutherobin, Desaetyleleutherobin, lsoeleutherobin A, and Z-Eleutherobin), Caribaeoside, Caribaeolin, Halichondrin B, D-64131 (Asta Medica), D-68144 (Asta Medica), Diazonamide A, A-293620 (Abbott), NPI-2350 (Nereus), Taccalonolide A, TUB-245 (Aventis), A-259754 (Abbott), Diozostatin, (−)-Phenylahistin (i.e. NSCL-96F037), D-68838 (Asta Medica), D-68836 (Asta Medica), Myoseverin B, D-43411 (Zentaris, i.e. D-81862), A-289099 (Abbott), A-318315 (Abbott), HTI-286 (i.e. SPA-110, trifluoroacetate salt) (Wyeth), D-82317 (Zentaris), D-82318 (Zentaris), SC-12983 (NCI), Resverastatin phosphate sodium, BPR-OY-007 (National Health Research Institutes), and SSR-250411 (Sanofi)), steroids (e.g., dexamethasone), finasteride, aromatase inhibitors, gonadotropin-releasing hormone agonists (GnRH) such as goserelin or leuprolide, adrenocorticosteroids (e.g., prednisone), progestins (e.g., hydroxyprogesterone caproate, megestrol acetate, medroxyprogesterone acetate), estrogens (e.g., diethylstilbestrol, ethinyl estradiol), antiestrogen (e.g., tamoxifen), androgens (e.g., testosterone propionate, fluoxymesterone), antiandrogen (e.g., flutamide), immunostimulants (e.g., *Bacillus* Calmette-Guerin (BCG), levamisole, interleukin-2, alpha-interferon, etc.), monoclonal antibodies (e.g., anti-CD20, anti-HER2, anti-CD52, anti-HLA-DR, and anti-VEGF monoclonal antibodies), immunotoxins (e.g., anti-CD33 monoclonal antibody-calicheamicin conjugate, anti-CD22 monoclonal antibody-pseudomonas exotoxin conjugate, etc.), radioimmunotherapy (e.g., anti-CD20 monoclonal antibody conjugated to $^{111}$In, $^{90}$Y, or $^{131}$I, etc.), triptolide, homoharringtonine, dactinomycin, doxorubicin, epirubicin, topotecan, itraconazole, vindesine, cerivastatin, vincristine, deoxyadenosine, sertraline, pitavastatin, irinotecan, clofazimine, 5-nonyloxytryptamine, vemurafenib, dabrafenib, erlotinib, gefitinib, EGFR inhibitors, epidermal growth factor receptor (EGFR)-targeted therapy or therapeutic (e.g. gefitinib (Iressa™), erlotinib (Tarceva™), cetuximab (Erbitux™), lapatinib (Tykerb™), panitumumab (Vectibix™), vandetanib (Caprelsa™), afatinib/BIBW2992, CI-1033/canertinib, neratinib/HKI-272, CP-724714, TAK-285, AST-1306, ARRY334543, ARRY-380, AG-1478, dacomitinib/PF299804, OSI-420/desmethyl erlotinib, AZD8931, AEE788, pelitinib/EKB-569, CUDC-101, WZ8040, WZ4002, WZ3146, AG-490, XL647, PD153035, BMS-599626), sorafenib, imatinib, sunitinib, dasatinib, or the like. In embodiments, the compositions herein may be used in combination with adjunctive agents that may not be effective alone, but may contribute to the efficacy of the active agent in treating cancer.

IL-6

IL-6 is an inflammation-associated cytokine produced primarily by tumor cells, tumor stroma and tumor-associated myeloid cells (Heikkila et al, European journal of cancer 2008; 44:937-45). Despite the well documented role for the IL-6-STAT3 axis in promoting tumor growth through its direct activities on tumor cells, little is known about the role IL-6 plays in immune modulation in cancer patients. To interrogate the effects of cancer on IL-6 immune biology, STAT signaling responses to IL-6 were examined in breast cancer patient PBMC populations. In response to IL-6, compared with healthy individuals, T cells from breast cancer patients were found to be defective in their ability to phosphorylate both STAT1 and STAT3. Importantly, there was lower individual and combined expression of the IL-6 receptor complex components, gp130 and IL-6Rα, in T cells from breast cancer patients compared with healthy controls. Thus, modulation of IL-6 pathway regulators, particularly the lower expression of the IL-6R complex, contributes to the loss of IL-6 responsiveness in breast cancer patient immune cells.

The tumor microenvironment is considered to be a chronically inflamed setting. IL-6 is systemically upregulated in cancer and IL-6 levels negatively associate with the survival of patients with various cancer types (Salgado et al, Int J Cancer 2003; 103:642-6; Hoejberg et al, Melanoma research 2012; 22:327-33; Knupfer et al, International journal of colorectal disease 2010; 25:135-40; Guo et al, Cancer treatment reviews 2012; 38:904-1017,22-24). In healthy adults, IL-6 circulation levels over 10 pg/ml are considered abnormally elevated (Heikkila et al, European journal of cancer 2008; 44:937-45).

The inventors have unexpectedly discovered that IL-6 signaling responses were defective in breast cancer patients with normal IL-6 plasma level, indicating that IL-6 related immune function is dysregulated in cancer patients with normal IL-6 circulation levels.

Within the tumor microenvironment, IL-6 is well-established as a pro-tumor cytokine and high expression levels of IL-6 are found within human breast cancer tumors (Knupfer et al, Breast cancer research and treatment 2007; 102:129-35; Dethlefsen et al, Breast cancer research and treatment 2013; 138:657-64; Chang et al, Neoplasia 2013; 15:848-62). Previous studies demonstrated that chronic exposure to IL-6 causes reduced levels of gp130 on T cells (Wang et al, Blood 1998; 91:3308-14; Hidalgo et al, Arthritis and rheumatism 2011; 63:3284-93; Oberg et al, Int Immunol 2006; 18:555-63). It was also reported that steroid hormones were able to affect IL-6 signaling pathway (Canellada et al, J Steroid Biochem Mol Biol 2008; 111:255-61).

The inventors found that the two chains of the IL-6 receptor complex were reduced via two distinct mechanisms: gp130 via reduced transcription, and IL-6Rα via enhanced cleavage by ADAM17. gp130 cytokines have pleiotropic roles in immune cell functions while the effects of gp130 deficiencies in the immune compartment in cancer models have not to our knowledge been studied. Thus, downregulation of gp130 expression may result in loss of the pleiotropic balance of gp130 cytokine responses in immune cells, the outcome of which will also depend on the integration of responses to other differentially expressed cytokines and aberrant signaling pathways.

IL-6 functions include promoting T cell survival, mediating helper T cell differentiation decisions by promoting Th2 over Th1 induction and Th17 over Treg induction, and regulating chemokine receptor expression, thereby influencing T cell recruitment to tissues (Dienz et al, Clinical immunology 2009; 130:27-33; Silver et al, J Leukoc Biol 2010; 88:1145-56). Therefore, loss of IL-6 responses may result in dysfunctional T cell survival as well as altered helper T cell differentiation and recruitment during inflammatory conditions. In the presence of IL-6 and TGFβ and IL-1β, naïve T cells can differentiate into Th17 cells, which are characterized by expression of the master transcription factor RORγt (Bailey et al, Frontiers in immunology 2014; 5:276). Th17 cells are found to negatively correlate with the presence of Treg cells and positively correlate with effector immune cells, including cytotoxic $CD8^+$ T cells and NK cells (Kryczek et al, Blood 2009; 114:1141-9; Zou et al, Nature reviews Immunology 2010; 10:248-56). The anti-tumor role of Th17 cells is at least partially due to their capacity to recruit effector cytotoxic T cells.

The inventors' findings that Th17 differentiations from $CD4^+$ naïve T cells from breast cancer patients were defective and correlated with IL-6 signaling responses suggest that IL-6 response in peripheral T cell may be linked with the Th17/Treg differentiation in breast cancer patients.

Since breast cancer is a heterogeneous disease with varied presentation, morphology and clinical behavior, a major challenge is the outcome prediction for early stage breast cancer patients. Currently, the risk of breast cancer progression is evaluated based on clinical and pathologic parameters (Rakha et al, Journal of clinical pathology 2013; 66:458-64) which can only be obtained after invasive biopsy or surgery and have limited predictive power.

More informative prognostic tests for breast cancer patients at diagnosis are needed. In this disclosure, the inventors demonstrate that IL-6 signaling responses predict clinical outcome which indicates that IL-6 signaling responses in peripheral T cells can be used as noninvasive blood-based predictive biomarkers for breast cancer patient outcomes.

The disclosure provides methods of detecting IL-6 activity in breast cancer patients, the method comprising (i) obtaining a biological sample comprising T cells from the patient; (ii) contacting the biological sample with an IL-6 pathway detection agent capable of binding an IL-6 pathway protein, thereby forming a detectable complex; and (iv) detecting and/or quantifying the detectable complex, thereby detecting IL-6 activity in the breast cancer patient. In embodiments, the methods further comprising treating the breast cancer patient. In embodiments, the breast cancer patient is a breast cancer patient in remission. In embodiments, the blood biological sample is a blood sample. In embodiments, the biological sample is a peripheral blood sample. In embodiments, the biological sample is a peripheral blood mononuclear cell sample. In embodiments, the T cells are peripheral blood T cells. In embodiments, the T cells are $CD4^+$ T cells. In embodiments, the T cells are naïve $CD4^+$ T cells. In embodiments, the biological sample is a peripheral blood sample, and the T cells are $CD4^+$ T cells. In embodiments, the biological sample is a peripheral blood mononuclear cell sample, and the T cells are naïve $CD4^+$ T cells.

In embodiments, the methods further comprising (i) analyzing the IL-6 activity in the breast cancer patient; (ii) comparing the IL-6 activity in the breast cancer patient to a control; and (iii) identifying whether there are defects in IL-6 signaling activity in the breast cancer patient. In embodiments, the breast cancer patient is a breast cancer patient in remission. A defect in IL-6 signaling activity is predictive of a higher possibility of relapse in a breast cancer patient in remission. In the event there is a prediction of breast cancer relapse, the methods further comprise treating the breast cancer patient in relapse, which may constitute any clinically appropriate treatment, such as monitoring for breast cancer relapse and/or the initiation of breast cancer treatment, such as hormone replacement therapy, chemotherapeutic agents, radiation therapy, surgery, or a combination of two or more thereof. In embodiments, the control is a healthy patient or healthy patient population. In embodiments, the control is a breast cancer patient in remission that has not relapsed, or a breast cancer patient population in remission that has not relapsed.

By detecting and/or quantifying the levels of IL-6 pathway proteins, IL-6 signaling activity can be identified, including whether the IL-6 signaling activity is normal or defective. For example, IL-6 induces phosphorylation of STAT. The inventors have discovered that the levels of phosphorylated STAT (e.g., phosphorylated STAT1 and phosphorylated STAT3) in T cells are lower in breast cancer patients in remission who relapse when compared to the levels of phosphorylated STAT in T cells in healthy controls or the levels of phosphorylated STAT in T cells in breast cancer patients in remission who do not relapse. Thus, lower levels of phosphorylated STAT in T cells indicate a defect in IL-6 signaling activity, which is caused by an upstream disruption in the IL-6 signaling pathway. Similarly, detecting and/or quantifying the levels of other IL-6 pathway proteins can identify whether there are any defects in IL-6 signaling activity. Such defects in IL-6 signaling activity would be predictive of breast can relapse for a breast cancer patient in remission.

In embodiments of the methods detecting IL-6 activity in breast cancer patients by contacting the biological sample with an IL-6 pathway detection agent capable of binding an IL-6 pathway protein, the IL-6 pathway protein is any protein in the IL-6 signaling pathway. In embodiments, the IL-6 pathway protein is STAT, phosphorylated STAT, gp130, ADAM 17, IL-6Rα, JAK, SOCS3, E3 ubiquitin ligase, protein tyrosine phosphatase, E3 SUMO-protein ligase, or a combination of two or more thereof. In embodiments, the IL-6 pathway protein is phosphorylated STAT, gp130, ADAM 17, IL-6Rα, JAK, SOCS3, E3 ubiquitin ligase, protein tyrosine phosphatase, E3 SUMO-protein ligase, or a combination of two or more thereof. In embodiments, the IL-6 pathway protein is phosphorylated STAT, wherein the phosphorylated STAT can be phosphorylated STAT1, phosphorylated STAT3, or a combination thereof. In embodiments, the IL-6 pathway protein is gp130. In embodiments, the IL-6 pathway protein is IL-6Rα.

The disclosure provides methods of detecting IL-6 activity in breast cancer patients, the method comprising (i) obtaining a biological sample comprising T cells from the patient; (ii) contacting the biological sample with an IL-6 pathway probe capable of hybridizing an IL-6 pathway mRNA expression sequence, thereby forming a hybridization complex; and (iv) detecting and/or quantifying the hybridization complex, thereby detecting IL-6 activity in the breast cancer patient. In embodiments, the breast cancer patient is a breast cancer patient in remission. In embodiments, the methods further comprising treating the breast cancer patient. In embodiments, the blood biological sample is a blood sample. In embodiments, the biological sample is a peripheral blood sample. In embodiments, the biological sample is a peripheral blood mononuclear cell sample. In embodiments, the T cells are peripheral blood T cells. In embodiments, the T cells are CD4$^+$ T cells. In embodiments, the T cells are naïve CD4$^+$ T cells. In embodiments, the biological sample is a peripheral blood sample, and the T cells are CD4$^+$ T cells. In embodiments, the biological sample is a peripheral blood mononuclear cell sample, and the T cells are naïve CD4$^+$ T cells.

In embodiments, the methods further comprising (i) analyzing the IL-6 activity in the breast cancer patient; (ii) comparing the IL-6 activity in the breast cancer patient to a control; and (iii) identifying whether there are defects in IL-6 signaling activity in the breast cancer patient. In the event, there are defects in IL-6 signaling activity, the methods further comprising predicting breast cancer relapse in a breast cancer patient in remission. In the event there is a prediction of breast cancer relapse, the methods further comprise treating the breast cancer patient in relapse, which may constitute any clinically appropriate treatment, such as more frequent monitoring for breast cancer relapse and/or the initiation of breast cancer treatment, such as hormone replacement therapy, chemotherapeutic agents, radiation therapy, or a combination of two or more thereof. In embodiments, the control is a healthy patient or healthy patient population. In embodiments, the control is a breast cancer patient in remission that has not relapsed, or a breast cancer patient population in remission that has not relapsed.

By detecting and/or quantifying the levels of IL-6 pathway mRNA expression sequences, IL-6 signaling activity can be identified, including whether the IL-6 signaling activity is normal or defective. For example, IL-6Rα on the cell surface is known to be subjected to proteolytic cleavage by a metallopeptidase ADAM 17. The inventors have discovered that the mRNA levels of ADAM17 in T cells are significantly higher in breast cancer patients in remission who relapse when compared to the mRNA levels of ADAM17 in T cells in healthy controls or the mRNA levels of ADAM17 in T cells in breast cancer patients in remission who do not relapse. Thus, elevated mRNA levels of ADAM17 in T cells indicate a defect in IL-6 signaling activity, which causes a disruption in the IL-6 signaling pathway Similarly, detecting and/or quantifying the levels of other IL-6 pathway mRNA expression sequences can identify whether there are any defects in IL-6 signaling activity. Such defects in IL-6 signaling activity would be predictive of breast can relapse for a breast cancer patient in remission.

In embodiments of the methods detecting IL-6 activity in breast cancer patients by contacting the biological sample with an IL-6 pathway probe capable of hybridizing an IL-6 pathway mRNA expression sequence, the IL-6 pathway mRNA expression sequence is any mRNA expression sequence in the IL-6 signaling pathway. In embodiments, the IL-6 pathway mRNA expression sequence is phosphorylated STAT, gp130, ADAM 17, IL-6Rα, JAK, SOCS3, E3 ubiquitin ligase, protein tyrosine phosphatase, E3 SUMO-protein ligase, or a combination of two or more thereof. In embodiments, the IL-6 pathway mRNA expression sequence is ADAM17. In embodiments, the IL-6 pathway mRNA expression sequence is gp130.

The disclosure provides methods of detecting IL-6 activity in breast cancer patients, the method comprising (i) obtaining a biological sample comprising T cells from the patient; (ii) isolating the T cells from the biological sample; (iii) culturing the T cells, thereby forming a T cell culture; and (iv) detecting one or more of the following in the T cell culture: Th17 cell levels, regulatory T cell (Treg) levels, Th2 cell levels, Th1 cell levels, IL-17 levels, or a combination of two or more thereof, thereby detecting IL-6 activity in the breast cancer patient. In embodiments, the methods comprising detecting Th17 cell levels. In embodiments, the methods comprising detecting regulatory T cell (Treg) levels. In embodiments, the methods comprising detecting Th2 cell levels. In embodiments, the methods comprising detecting Th1 cell levels. In embodiments, the methods comprising detecting IL-17 levels. In embodiments, the breast cancer patient is a breast cancer patient in remission. In embodiments, the methods further comprising treating the breast cancer patient. In embodiments, the blood biological sample is a blood sample. In embodiments, the biological sample is a peripheral blood sample. In embodiments, the biological sample is a peripheral blood mononuclear cell sample. In embodiments, the T cells are peripheral blood T cells. In embodiments, the T cells are CD4$^+$ T cells. In embodiments, the T cells are naïve CD4$^+$ T cells. In embodiments, the biological sample is a peripheral blood sample, and the T cells are CD4$^+$ T cells. In embodiments, the biological sample is a peripheral blood mononuclear cell sample, and the T cells are naïve CD4$^+$ T cells. Methods for isolating and culturing T cells are well known in the art, e.g., Raulf-Heimsoth, Methods Mol. Med., 138:17-30 (2008).

In embodiments, the methods further comprising (i) analyzing the IL-6 activity in the breast cancer patient; (ii) comparing the IL-6 activity in the breast cancer patient to a control; and (iii) identifying whether there are defects in IL-6 signaling activity in the breast cancer patient. In the event there are defects in IL-6 signaling activity, the methods further comprising predicting breast cancer relapse in a breast cancer patient in remission. In the event there is a prediction of breast cancer relapse, the methods further comprise treating the breast cancer patient in relapse, which may constitute any clinically appropriate treatment, such as more frequent monitoring for breast cancer relapse and/or the initiation of breast cancer treatment, such as hormone replacement therapy, chemotherapeutic agents, radiation therapy, or a combination of two or more thereof. In embodiments, the control is a healthy patient or healthy patient population. In embodiments, the control is a breast cancer patient in remission that has not relapsed, or a breast cancer patient population in remission that has not relapsed.

By detecting and/or quantifying Th17 cell levels, regulatory T cell (Treg) levels, Th2 cell levels, Th1 cell levels, IL-17 levels, or a combination of two or more thereof, IL-6 signaling activity can be identified, including whether the IL-6 signaling activity is normal or defective. For example, the inventors have discovered that defective IL-6 responses were associated with blunted Th17 differentiation from CD4$^+$ naïve T cells. Thus, there are lower levels of Th17 cells in breast cancer patients in remission who relapse when compared to the levels of Th17 cells in healthy controls or the levels of Th17 cells in breast cancer patients in remission who do not relapse. Thus, reduced Th17 levels indicate a defect in IL-6 signaling activity.

The disclosure provides methods of treating an IL-6 pathway-defective patient, wherein the patient is a breast cancer remission patient, the method comprising administering a therapeutically effective amount of an anti-cancer agent to the patient. The disclosure provides methods of treating an IL-6 activity-defective patient, wherein the patient is a breast cancer remission patient, the method comprising administering a therapeutically effective amount of an anti-cancer agent to the patient. Methods of detecting the IL-6 activity of the patient are described herein. If the patient has defective IL-6 activity, then the patient has a defective IL-6 pathway.

The disclosure provides methods of predicting relapse in a breast cancer patient that is in remission, the method comprising (i) obtaining a biological sample comprising T cells from the patient; (ii) contacting the biological sample with an IL-6 pathway detection agent capable of binding an IL-6 pathway protein or an IL-6 pathway mRNA expression sequence, thereby forming a detectable complex; and (iv) detecting and/or quantifying the detectable complex, thereby detecting IL-6 activity in the breast cancer patient; wherein a different IL-6 activity relative to a standard control indicates an increased probability of breast cancer relapse in the breast cancer patient relative to a breast cancer patient without the different IL-6 activity. In embodiments, the different IL-6 activity is decreased IL-6 signaling activity relative to a standard control.

In embodiments of the disclosure, breast cancer patients (e.g., newly diagnosed or relapsed) and breast cancer patients in remission can be treated for breast cancer using therapy known in the art. Exemplary therapies include hormone replacement therapy, chemotherapeutic agents, radiation therapy, and a combination of two or more thereof.

Embodiments 1 to 82

Embodiment 1

A method of detecting IL-6 activity in a breast cancer patient, the method comprising (i) obtaining a biological sample comprising T cells from the patient; (ii) contacting the biological sample with an IL-6 pathway detection agent capable of binding an IL-6 pathway protein, thereby forming a detectable complex; and (iii) detecting and/or quantifying the detectable complex, thereby detecting IL-6 activity in the breast cancer patient.

Embodiment 2

The method of Embodiment 1, wherein the breast cancer patient is in remission.

Embodiment 3

The method of Embodiment 1 or 2, wherein the biological sample is a blood sample.

Embodiment 4

The method of any one of Embodiments 1-3, wherein the biological sample is a peripheral blood sample.

Embodiment 5

The method of any one of Embodiments 1-4, wherein the biological sample is peripheral blood mononuclear cell sample.

Embodiment 6

The method of any one of Embodiments 1-5, wherein the T cells are peripheral blood T cells.

Embodiment 7

The method of any one of Embodiments 1-6, wherein the T cells are CD4$^+$ T cells.

Embodiment 8

The method of any one of Embodiments 1-7, wherein the T cells are naïve CD4$^+$ T cells.

Embodiment 9

The method of any one of Embodiments 1-8, wherein the IL-6 pathway protein is phosphorylated STAT, gp130, ADAM 17, IL-6Rα, Jak, SOCS3, E3 ubiquitin ligase, protein tyrosine phosphatase, E3 SUMO-protein ligase, or a combination of two or more thereof.

Embodiment 10

The method of any one of Embodiments 1-9, wherein the IL-6 pathway protein is phosphorylated STAT, IL-6Rα, gp130, ADAM 17, or a combination thereof.

Embodiment 11

The method of any one of Embodiments 1-10, wherein the IL-6 pathway protein is phosphorylated STAT.

Embodiment 12

The method of any one of Embodiments 9-11, wherein the phosphorylated STAT is phosphorylated STAT1, phosphorylated STAT3, or a combination thereof.

Embodiment 13

The method of any one of Embodiments 1-12, further comprising monitoring the patient for breast cancer relapse.

Embodiment 14

The method of any one of Embodiments 1-13, further comprising administering to the patient an anti-cancer agent.

Embodiment 15

The method of Embodiment 14, wherein the anti-cancer agent is a hormone replacement therapy, a chemotherapeutic agent, radiation therapy, or a combination of two or more thereof.

Embodiment 16

A method of detecting IL-6 activity in a breast cancer patient, the method comprising (i) obtaining a biological sample comprising T cells from the patient; (ii) contacting the biological sample with an IL-6 pathway probe capable of hybridizing an IL-6 pathway mRNA expression sequence, thereby forming a hybridization complex; and (iii) detecting and/or quantifying the hybridization complex, thereby detecting IL-6 activity in the breast cancer patient.

Embodiment 17

The method of Embodiment 16, wherein the breast cancer patient is in remission.

Embodiment 18

The method of Embodiment 16 or 17, wherein the biological sample is a blood sample.

Embodiment 19

The method of any one of Embodiments 16-18, wherein the biological sample is a peripheral blood sample.

Embodiment 20

The method of any one of Embodiments 16-19, wherein the biological sample is peripheral blood mononuclear cell sample.

Embodiment 21

The method of any one of Embodiments 16-20, wherein the T cells are peripheral blood T cells.

Embodiment 22

The method of any one of Embodiments 16-21, wherein the T cells are CD4$^+$ T cells.

Embodiment 23

The method of any one of Embodiments 16-22, wherein the T cells are naïve CD4$^+$ T cells.

Embodiment 24

The method of any one of Embodiments 16-23, wherein the IL-6 pathway mRNA expression sequence is phosphorylated STAT, gp130, ADAM 17, IL-6Rα, Jak, SOCS3, E3 ubiquitin ligase, protein tyrosine phosphatase, E3 SUMO-protein ligase, or a combination of two or more thereof.

Embodiment 25

The method of any one of Embodiments 16-24, wherein the IL-6 pathway mRNA expression sequence is phosphorylated STAT, IL-6Rα, gp130, ADAM 17, or a combination thereof.

Embodiment 26

The method of any one of Embodiments 16-25, wherein the IL-6 pathway mRNA expression sequence is gp130.

Embodiment 27

The method of any one of Embodiments 16-26, further comprising monitoring the patient for breast cancer relapse.

Embodiment 28

The method of any one of Embodiments 16-27, further comprising administering to the patient an anti-cancer agent.

Embodiment 29

The method of Embodiment 28, wherein the anti-cancer agent is a hormone replacement therapy, a chemotherapeutic agent, radiation therapy, or a combination of two or more thereof.

Embodiment 30

A method of detecting IL-6 activity in a breast cancer patient, the method comprising (i) obtaining a biological sample comprising T cells from the patient; (ii) isolating the T cells from the biological sample; (iii) culturing the T cells, thereby forming a T cell culture; and (iv) detecting levels of one or more of the following in the T cell culture: Th17 cells, regulatory T cells (Treg), Th2 cells, Th1 cells, IL-17s, or a combination of two or more thereof, thereby detecting IL-6 activity in the breast cancer patient.

Embodiment 31

The method of Embodiment 30, wherein the breast cancer patient is in remission.

Embodiment 32

The method of Embodiment 30 or 31, wherein the biological sample is a blood sample.

Embodiment 33

The method of any one of Embodiments 30-32, wherein the biological sample is a peripheral blood sample.

Embodiment 34

The method of any one of Embodiments 30-33, wherein the biological sample is peripheral blood mononuclear cell sample.

Embodiment 35

The method of any one of Embodiments 30-34, wherein the T cells are peripheral blood T cells.

Embodiment 36

The method of any one of Embodiments 30-35, wherein the T cells are CD4$^+$ T cells.

Embodiment 37

The method of any one of Embodiments 30-36, wherein the T cells are naïve CD4$^+$ T cells.

Embodiment 38

The method of any one of Embodiments 30-37, wherein step (iv) comprises detecting Th17 cells, thereby detecting IL-6 activity in the breast cancer patient.

Embodiment 39

The method of any one of Embodiments 30-38, wherein step (iv) comprises detecting IL-17 levels, thereby detecting IL-6 activity in the breast cancer patient.

Embodiment 40

The method of any one of Embodiments 30-39, wherein step (iv) comprises detecting regulatory T cells, thereby detecting IL-6 activity in the breast cancer patient.

Embodiment 41

The method of any one of Embodiments 30-40, wherein step (iv) comprises detecting Th2 cells, thereby detecting IL-6 activity in the breast cancer patient.

Embodiment 42

The method of any one of Embodiments 30-41, wherein step (iv) comprises detecting Th1 cells, thereby detecting IL-6 activity in the breast cancer patient.

Embodiment 43

The method of any one of Embodiments 30-42, further comprising monitoring the patient for breast cancer relapse.

Embodiment 44

The method of any one of Embodiments 30-43, further comprising administering an anti-cancer agent to the patient.

Embodiment 45

The method of Embodiment 44, wherein the anti-cancer agent is a hormone replacement therapy, a chemotherapeutic agent, radiation therapy, or a combination of two or more thereof.

Embodiment 46

A method of treating an IL-6 pathway defective patient, wherein the patient is a breast cancer remission patient, the method comprising administering to the patient a therapeutically effective amount of an anti-cancer agent.

Embodiment 47

The method of Embodiment 46, wherein the anti-cancer agent is a hormone replacement therapy, a chemotherapeutic agent, radiation therapy, or a combination of two or more thereof.

Embodiment 48

The method of Embodiment 46 or 47, further comprising detecting IL-6 activity in the patient following the method of any one of Embodiments 1-26 and 30-42.

Embodiment 49

A solid support comprising one or more IL-6 pathway detection agents capable of binding an IL-6 pathway protein.

Embodiment 50

The solid support of Embodiment 49, wherein the IL-6 pathway protein is phosphorylated STAT, gp130, ADAM 17, IL-6Rα, Jak, SOCS3, E3 ubiquitin ligase, protein tyrosine phosphatase, E3 SUMO-protein ligase, or a combination of two or more thereof.

Embodiment 51

The solid support of Embodiment 49 or 50, wherein the IL-6 pathway protein is phosphorylated STAT, IL-6Rα, gp130, ADAM 17, or a combination thereof.

Embodiment 52

The solid support of any one of Embodiments 49-51, wherein the IL-6 pathway protein is phosphorylated STAT.

Embodiment 53

The solid support of any one of Embodiments 49-52, wherein the phosphorylated STAT is phosphorylated STAT1, phosphorylated STAT3, or a combination thereof.

Embodiment 54

The solid support of any one of Embodiments 49-53, wherein the solid support only comprises one or more IL-6 pathway detection agents capable of binding an IL-6 pathway protein.

Embodiment 55

A solid support comprising one or more IL-6 pathway probes capable of hybridizing an IL-6 pathway mRNA expression sequence.

Embodiment 56

The solid support of Embodiment 55, wherein the IL-6 pathway mRNA expression sequence is phosphorylated STAT, gp130, ADAM 17, IL-6Rα, Jak, SOCS3, E3 ubiquitin ligase, protein tyrosine phosphatase, E3 SUMO-protein ligase, or a combination of two or more thereof.

Embodiment 57

The solid support of Embodiment 55 or 56, wherein the IL-6 pathway mRNA expression sequence is phosphorylated STAT, gp130, ADAM 17, IL-6Rα, or a combination of two or more thereof.

Embodiment 58

The solid support of any one of Embodiments 55-57, wherein the IL-6 pathway mRNA expression sequence is gp130.

Embodiment 59

The solid support of any one of Embodiments 55-48, wherein the solid support only comprises one or more IL-6 pathway probes capable of hybridizing an IL-6 pathway mRNA expression sequence.

Embodiment 60

A method of predicting relapse in a breast cancer patient in remission, the method comprising (i) obtaining a biological sample comprising T cells from the patient; (ii) contacting the biological sample with an IL-6 pathway detection agent capable of binding an IL-6 pathway protein, thereby forming a detectable complex; and (iii) detecting and/or quantifying the detectable complex, thereby detecting IL-6 activity in the breast cancer patient; wherein a different IL-6 activity relative to a standard control indicates an increased probability of breast cancer relapse in the breast cancer patient relative to a breast cancer patient without the different IL-6 activity.

Embodiment 61

The method of Embodiment 60, wherein the different IL-6 activity is a lowered IL-6 activity.

Embodiment 62

The method of Embodiment 60 or 61, wherein the biological sample is a blood sample.

Embodiment 63

The method of any one of Embodiments 60-62, wherein the biological sample is a peripheral blood sample.

Embodiment 64

The method of any one of Embodiments 60-63, wherein the biological sample is peripheral blood mononuclear cell sample.

Embodiment 65

The method of any one of Embodiments 60-64, wherein the T cells are peripheral blood T cells.

Embodiment 66

The method of any one of Embodiments 60-65, wherein the T cells are CD4$^+$ T cells.

Embodiment 67

The method of any one of Embodiments 60-66, wherein the T cells are naïve CD4$^+$ T cells.

Embodiment 68

The method of any one of Embodiments 60-67, wherein the IL-6 pathway protein is phosphorylated STAT, gp130, ADAM 17, IL-6Rα, Jak, SOCS3, E3 ubiquitin ligase, protein tyrosine phosphatase, E3 SUMO-protein ligase, or a combination of two or more thereof.

Embodiment 69

The method of any one of Embodiments 60-68, wherein the IL-6 pathway protein is phosphorylated STAT, IL-6Rα, gp130, ADAM 17, or a combination thereof.

Embodiment 70

The method of any one of Embodiments 60-69, wherein the IL-6 pathway protein is phosphorylated STAT.

Embodiment 71

The method of any one of Embodiments 60-70, wherein the phosphorylated STAT is phosphorylated STAT1, phosphorylated STAT3, or a combination thereof.

Embodiment 72

A method of predicting relapse in a breast cancer patient in remission, the method comprising (i) obtaining a biological sample comprising T cells from the patient; (ii) contacting the biological sample with an IL-6 pathway probe capable of hybridizing an IL-6 pathway mRNA expression sequence, thereby forming a hybridization complex; and (iii) detecting and/or quantifying the hybridization complex, thereby detecting IL-6 activity in the breast cancer patient; wherein a different IL-6 activity relative to a standard control indicates an increased probability of breast cancer relapse in the breast cancer patient relative to a breast cancer patient without the different IL-6 activity.

Embodiment 73

The method of Embodiment 72, wherein the different IL-6 activity is a lowered IL-6 activity.

Embodiment 74

The method of Embodiment 72 or 73, wherein the biological sample is a blood sample.

Embodiment 75

The method of any one of Embodiments 72-74, wherein the biological sample is a peripheral blood sample.

Embodiment 76

The method of any one of Embodiments 72-75, wherein the biological sample is peripheral blood mononuclear cell sample.

Embodiment 77

The method of any one of Embodiments 72-76, wherein the T cells are peripheral blood T cells.

Embodiment 78

The method of any one of Embodiments 72-77, wherein the T cells are CD4$^+$ T cells.

Embodiment 79

The method of any one of Embodiments 72-78, wherein the T cells are naïve CD4$^+$ T cells.

Embodiment 80

The method of any one of Embodiments 72-79, wherein the IL-6 pathway mRNA expression sequence is phosphorylated STAT, gp130, ADAM 17, IL-6Rα, Jak, SOCS3, E3 ubiquitin ligase, protein tyrosine phosphatase, E3 SUMO-protein ligase, or a combination of two or more thereof.

Embodiment 81

The method of any one of Embodiments 72-80, wherein the IL-6 pathway mRNA expression sequence is phosphorylated STAT, IL-6Rα, gp130, ADAM 17, or a combination thereof.

Embodiment 82

The method of any one of Embodiments 72-81, wherein the IL-6 pathway mRNA expression sequence is gp130.

Embodiments N1 to N20

Embodiment N1

A method of detecting IL-6 activity in a breast cancer patient, the method comprising the steps of: (i) obtaining a biological sample comprising T cells from the patient; (ii) contacting the biological sample with either: (a) an IL-6 pathway detection agent capable of binding an IL-6 pathway protein, thereby forming a detectable complex; or (b) an IL-6 pathway probe capable of hybridizing an IL-6 pathway mRNA expression sequence, thereby forming a hybridization complex; and (iii) detecting and/or quantifying either: (a) the detectable complex; or (b) the hybridization complex, respectively; thereby detecting IL-6 activity in the breast cancer patient

Embodiment N2

The method of Embodiment N1, wherein the breast cancer patient is in remission.

Embodiment N3

The method of Embodiment N1 or N2, wherein the biological sample is a blood sample.

Embodiment N4

The method of Embodiment N1 or N2, wherein the biological sample is a peripheral blood sample.

Embodiment N5

The method of Embodiment N1 or N2, wherein the biological sample is peripheral blood mononuclear cell sample.

Embodiment N6

The method of any one of Embodiments N1 to N5, wherein the T cells are peripheral blood T cells.

Embodiment N7

The method of any one of Embodiments N1 to N5, wherein the T cells are CD4$^+$ T cells.

Embodiment N8

The method of any one of Embodiments N1 to N5, wherein the T cells are naïve CD4$^+$ T cells.

Embodiment N9

The method of any one of Embodiments N1 to N8, wherein the IL-6 pathway protein is phosphorylated STAT, gp130, ADAM 17, IL-6Rα, Jak, SOCS3, E3 ubiquitin ligase, protein tyrosine phosphatase, E3 SUMO-protein ligase, or a combination of two or more thereof; and wherein the IL-6 pathway mRNA expression sequence is phosphorylated STAT, gp130, ADAM 17, IL-6Rα, Jak, SOCS3, E3 ubiquitin ligase, protein tyrosine phosphatase, E3 SUMO-protein ligase, or a combination of two or more thereof

Embodiment N10

The method of any one of Embodiments N1 to N8, wherein the IL-6 pathway protein is phosphorylated STAT, IL-6Rα, gp130, ADAM 17, or a combination thereof, and wherein the IL-6 pathway mRNA expression sequence is phosphorylated STAT, IL-6Rα, gp130, ADAM 17, or a combination thereof

Embodiment N11

The method of any one of Embodiments N1 to N8, wherein the IL-6 pathway protein is phosphorylated STAT.

Embodiment N12

The method of any one of Embodiments N1 to N8, wherein the IL-6 pathway protein is phosphorylated STAT1, phosphorylated STAT3, or a combination thereof.

Embodiment N13

The method of any one of Embodiments N1 to N8, wherein the IL-6 pathway mRNA expression sequence is gp130.

Embodiment N14

The method of any one of Embodiments N1 to N13, further comprising the steps of: (i) monitoring the patient for breast cancer relapse; (ii) administering to the patient an anti-cancer agent; or (iii) monitoring the patient for breast cancer relapse and administering to the patient an anti-cancer agent

Embodiment N15

A method of detecting IL-6 activity in a breast cancer patient, the method comprising: (i) obtaining a biological sample comprising T cells from the patient; (ii) isolating the T cells from the biological sample; (iii) culturing the T cells, thereby forming a T cell culture; and (iv) detecting levels of one or more of the following in the T cell culture: Th17 cells, regulatory T cells (Treg), Th2 cells, Th1 cells, IL-17s, or a combination of two or more thereof; thereby detecting IL-6 activity in the breast cancer patient.

Embodiment N16

A method of treating an IL-6 pathway defective patient, wherein the patient is a breast cancer remission patient, the method comprising administering to the patient a therapeutically effective amount of an anti-cancer agent

Embodiment N17

A solid support comprising: (i) one or more IL-6 pathway detection agents capable of binding an IL-6 pathway protein; or (ii) one or more IL-6 pathway probes capable of hybridizing an IL-6 pathway mRNA expression sequence.

Embodiment N18

The solid support of Embodiment N17, wherein the IL-6 pathway protein is phosphorylated STAT, gp130, ADAM 17, IL-6Rα, Jak, SOCS3, E3 ubiquitin ligase, protein tyrosine phosphatase, E3 SUMO-protein ligase, or a combination of two or more thereof; and wherein the IL-6 pathway mRNA expression sequence is phosphorylated STAT, gp130, ADAM 17, IL-6Rα, Jak, SOCS3, E3 ubiquitin ligase, protein tyrosine phosphatase, E3 SUMO-protein ligase, or a combination of two or more thereof.

Embodiment N19

The solid support of Embodiment N17 or N18, wherein the solid support only comprises: (i) one or more IL-6 pathway detection agents capable of binding an IL-6 pathway protein; or (ii) one or more IL-6 pathway probes capable of hybridizing an IL-6 pathway mRNA expression sequence.

Embodiment N20

Amethod of predicting relapse in a breast cancer patient in remission, the method comprising: (i) obtaining a biological sample comprising T cells from the patient; (ii) contacting the biological sample with either: (a) an IL-6 pathway detection agent capable of binding an IL-6 pathway protein, thereby forming a detectable complex; or (b) an IL-6 pathway probe capable of hybridizing an IL-6 pathway mRNA expression sequence, thereby forming a hybridization complex (iii) detecting and/or quantifying: (a) the detectable complex, or (b) the hybridization complex, respectively; thereby detecting IL-6 activity in the breast cancer patient; wherein a different IL-6 activity relative to a standard control indicates an increased probability of breast cancer relapse in the breast cancer patient relative to a breast cancer patient without the different IL-6 activity

EXAMPLES

The following examples are for purposes of illustration and are not intended to limit the spirit or scope of the disclosure or claims.

IL-6 is a pleiotropic cytokine that plays various roles on modulating the activities of tumor and immune cells (Mantovani et al, Nature 2008; 454:436-44). IL-6 signals through the common gp130 receptor and the specific IL-6Rα co-receptor to activate the Janus kinase (JAK)-signal transducer and activator of transcription (STAT) signaling pathway (Heinrich et al, The Biochemical journal 2003; 374:1-20). Phosphorylated STATs dimerize and translocate into the nucleus to initiate transcription of IL-6 responsive genes (Naugler et al, Trends in molecular medicine 2008; 14:109-19).

Within the tumor microenvironment, not only macrophages, myeloid-derived suppressor cells (MDSC) and fibroblasts but also cancer cells produce IL-6 (Fisher et al, Seminars in immunology 2014; 26:38-47). IL-6 promotes survival and proliferation of cancer cells, drives chronic inflammation that supports tumor growth, and suppresses anti-tumor T cell activity (Fisher et al, Seminars in immunology 2014; 26:38-47; Taniguchi et al, Seminars in immunology 2014; 26:54-74; Yu et al, Nature reviews Cancer 2014; 14:736-46; DeNardo et al, Breast Cancer Res 2007; 9:212; Balkwill et al, Cancer Cell 2005; 7:211-7). On T cells, IL-6 functions to prevent apoptosis (Teague et al, J Immunol 1997; 158:5791-6; Takeda et al, J Immunol 1998; 161:4652-60) and skews naïve $CD4^+$ T cells away from becoming regulatory T (Treg) cells and towards becoming pro-inflammatory Th17 cells (Kimura et al, European journal of immunology 2010; 40:1830-5). IL-6 also regulates chemokine receptors expression to influence tissue recruitment of T cells (Hunter et al, Nat Immunol 2015; 16:448-57). Higher frequencies of Treg and exclusion of cytotoxic T cells from the tumor are both associated with poorer outcomes in cancer patients (Mahmoud et al, Journal of clinical oncology: official journal of the American Society of Clinical Oncology 2011; 29:1949-55; Bates et al, Journal of clinical oncology: official journal of the American Society of Clinical Oncology 2006; 24:5373-80). Thus, alterations in the response of T cells to IL-6 contributes to deficient anti-tumor responses. However, the mechanisms connecting IL-6 associated inflammation to dysfunctional anti-tumor immune responses have not previously been elucidated. Alterations in cytokine levels and the ability of immune cells to appropriately respond to cytokines are likely to contribute to immunologic abnormalities in cancer patients. The prominent association of IL-6 with both inflammation and cancer argues that this pleiotropic immunomodulatory cytokine serves as a link between cancer-associated inflammation and immune dysfunction In this regard, the inventors investigated the functionality of IL-6 signaling responses in peripheral blood T cells of breast cancer patients. By using phosphoflow cytometry, the inventors found that IL-6 induced phosphorylation of STAT1 and STAT3 were significantly lower in peripheral blood $CD4^+$ naïve T cells from breast cancer patients at diagnosis. To explore the mechanisms underlying defective responses of patient T cells to IL-6, expression levels of key components of the IL-6 signaling pathway were evaluated. Breast cancer patients had substantially decreased levels of the IL-6 co-receptors, gp130 and IL-6Rα, which further correlated with decreased responsiveness to IL-6. Interestingly, IL-6 plasma levels were not elevated in breast cancer patients at diagnosis and IL-6 signaling responses were independent of the IL-6 plasma levels. The inventors also found that defective IL-6 responses were associated with blunted Th17 differentiation from $CD4^+$ naïve T cells. Importantly, defective IL-6 signaling response significantly correlated with worse relapse-free survival, indicating the potential of IL-6 signaling response in peripheral blood T cells at diagnosis as a prognostic biomarker for breast cancer patients.

Provided herein is evidence that the IL-6 signaling response in peripheral blood T cells is impaired in breast cancer patients and is associated with blunted Th17 differentiation. In embodiments, downregulation of gp130 and IL-6Rα in breast cancer patients is independent of plasma IL-6 levels. Importantly, defective IL-6 signaling in peripheral blood T cells at diagnosis significantly may correlate with worse relapse-free survival. This disclosure provides evidence that, inter alia, intact IL-6 signaling in T cells are important for controlling cancer progression, and that the IL-6 signaling response in peripheral blood T cells, at diagnosis or in remission, is a predictive biomarker for clinical outcome of breast cancer patients.

Materials and Methods

All patient blood samples were collected prior to surgery or administration of any therapy. Age-matched healthy control peripheral blood samples were obtained from the Stanford Blood Center and City of Hope Blood Donor Center. All the blood from patients and healthy donors was drawn directly into heparin-coated vacutainer tubes (BD Biosciences, San Jose, Calif., USA). The study was approved by the Institutional Review Board of Stanford Medical Center and City of Hope Comprehensive Cancer Center.

Peripheral blood mononuclear cells (PBMCs) were collected by density gradient centrifugation using Ficoll-Paque and cryopreserved in 10% DMSO FBS. Cryopreserved PBMCs were thawed and rested overnight in RPMI-10% heat-inactivated FBS-lx Penicillin-Streptomycin-Glutamine at 37° C., 7.5% $CO_2$ prior to performing assays.

$0.5 \times 10^6$ PBMCs were aliquoted into individual wells of deep-well 96-well plates. Media or IL-6 (R&D Systems, Minneapolis, Minn., USA) was added to each well to obtain a final concentration of 100 ng/ml for IL-6. Cells were then incubated at 37° C. for 15 minutes followed by fixation with 1.5% paraformaldehyde (PFA) for 10 minutes at room temperature. Cells were washed with PBS to remove PFA, and permeabilized by the addition of 100% methanol. PBMCs were stored at −80° C. until antibody staining for flow cytometry analysis.

Permeabilized cells were thawed and washed three times with staining buffer (PBS/2% FBS/0.5% BSA) to remove methanol. Cells were resuspended in the same volume of staining buffer and staining antibodies were added. For assessment of pSTAT1 and pSTAT3, the following staining panel was utilized: CD3-V450 (UCHT1), CD4-PerCP-Cy5.5 (SK.3), CD45RA-PE-Cy7 (L48), CD8-V500 (RPA-T8), CD16-PE (3G8), CD20-PerCP-Cy5.5 (H1), CD33-PE-Cy7 (P67.6), pSTAT1 (pY701)-AF647 (4a), and pSTAT3 (pY705)-AF488 (4/P-STAT3) antibodies (BD Biosciences, San Jose, Calif., USA). Naïve CD4+ T cell population was determined by the following markers: CD3+CD4+ CD45RA+. The magnitude of each individual's pSTAT1 and pSTAT3 response to IL-6 was expressed as the IL-6 induced median fluorescence intensity (MFI) minus the unstimulated MFI for pSTAT1 and pSTAT3.

For assessment of intracellular total STAT1 and STAT3 levels, LIVE/DEAD Fixable Blue Dead Cell Stain (Life Technologies, Carlsbad, Calif., USA) was added to unstimulated cells for 30 minutes and washed away prior to PFA fixation and permeabilization. After washing the cells to remove methanol, the following staining panel was utilized: CD3-V500 (UCHT1), CD4-PerCP-Cy5.5 (SK.3), CD8-PacBlue (RPA-T8), CD45RA-PE-Cy7 (L48), CD62L-FITC (DREG-56), STAT1-AF647 (1/Stat1), and STAT3-PE (M59-50) antibodies (BD Biosciences). For assessment of gp130 and IL-6Rα expression levels on live PBMCs, the following staining panel was utilized: CD3-V500 (UCHT1), CD4-PerCP-Cy5.5 (SK.3), CD8-PacBlue (RPA-T8), CD45RA-PE-Cy7 (L48), CD62L-e605NC (DREG-56), gp130-PE (AM64) (BD Biosciences), and IL-6Rα-AF647 (BL-126) (Biolegend, San Diego, Calif., USA) antibodies, and LIVE/DEAD Fixable Blue Dead Cell Stain (Life Technologies). Expression of total STAT1, STAT3, gp130 and IL-6Rα was expressed by subtracting the MFI of isotype stains.

Flow cytometry was performed using FACS Canto, LSR II, or Fortessa Flow Cytometers (BD Biosciences). Flow cytometry data was analyzed using FlowJo software (Tree Star Inc., Ashland, Oreg., USA). t-tests were used to determine the statistical significance of breast cancer patient with healthy donors (Graphpad Prism, GraphPad Software, LaJolla, Calif., USA).

Plasma IL-6 ELISA

All patient plasma samples were collected prior to surgery or administration of any therapy. Plasma samples were kept frozen at −80° C. then thawed shortly before determination of IL-6 level. IL-6 levels were determined by high sensitivity ELISA (eBioscience, San Diego, Calif., USA) according to manufacturer's protocol.

RNA isolation and Quantitative Real Time PCR

Naïve CD4+ T cells were isolated from PBMCs with an enrichment kit (eBioscience). Total RNA was isolated from naïve CD4+ T cells using RNAzol® RT reagent (Molecular Research Center, Cincinnati, Ohio) according to the manufacture's instruction. cDNA was synthesized using $RT^2$ First Strand Kit (Qiagen, Valencia, Calif.). For Quantitative Real Time PCR (Q-PCR), $RT^2$ SYBR Green Master Mix (Qiagen) was used and Q-PCR was performed and analyzed using the CFX96 Real-Time PCR System (Bio-Rad, Hercules, Calif.). Gene expressions were normalized to GAPDH as an internal control and results are represented as fold change using the AACt method.

The following primer sequences were used in the reaction: 116r (F: TTGTTTGTGAGTGGGGTCCT (SEQ ID NO: 1); R: TGGGACTCCTGGGAATACTG (SEQ ID NO:2)), Il6st (F: AGGACCAAAGATGCCTCAAC (SEQ ID NO:3); R: GAATGAAGATCGGGTGGATG (SEQ ID NO:4)), Adam17 (F: ACTCTGAGGACAGTTAAC-CAAACC (SEQ ID NO:5); R: AGTAAAAGGAGC-CAATACCACAAG (SEQ ID NO:6)).

Th17 differentiation assay

Naïve CD4+ T cells were isolated from PBMCs with an enrichment kit (eBioscience). Cells were cultured in serum-free medium with anti-CD3/CD28 beads (Life Technologies), IL-6 (30 ng/ml), IL-1β (20 ng/ml) (eBioscience), IL-23 (30 ng/ml), TGF-β (2.25 ng/ml) (Peprotech, Rocky Hill, N.J., USA), anti-IFN-γ antibody (1 μg/ml) and anti-IL-4 antibody (2.5 μg/ml) (Biolegend) for 7 days. Supernatants were collected after 7 days and IL-17 levels were determined by ELISA (Biolegend). Cells were stimulated with ionomycin (1 μg/ml) (Life Technologies), Phorbol 12-myristate β-acetate (PMA) (50 ng/ml) (Sigma-Aldrich, St Louis, Mo., USA) and Brefeldin A (BFA) (5 μg/ml) (Biolegend) for 5 hrs and were analyzed by flow cytometry with anti-RORγt-AF647 (Q21-559) (BD Bioscience) and anti-IL-17A-FITC (BL168) (Biolegend) antibodies.

Statistical Analysis

Relapse-free survival was defined as the time from the date of diagnosis of breast cancer to the date of cancer recurrence. Kaplan-Meier method with log-rank test was used to determine IL-6 signaling responsiveness as prognostic factors for relapse-free survival of breast cancer patients. Multivariate Cox regression model analysis was performed to determine independence of prognostic factor. The correlation between IL-6 signaling response and clinicopathologic characteristics were evaluated with Pearson's correlation coefficient presented with r and p value. All tests with p value<0.05 were considered statistically significant.

Results

Figure 1B:
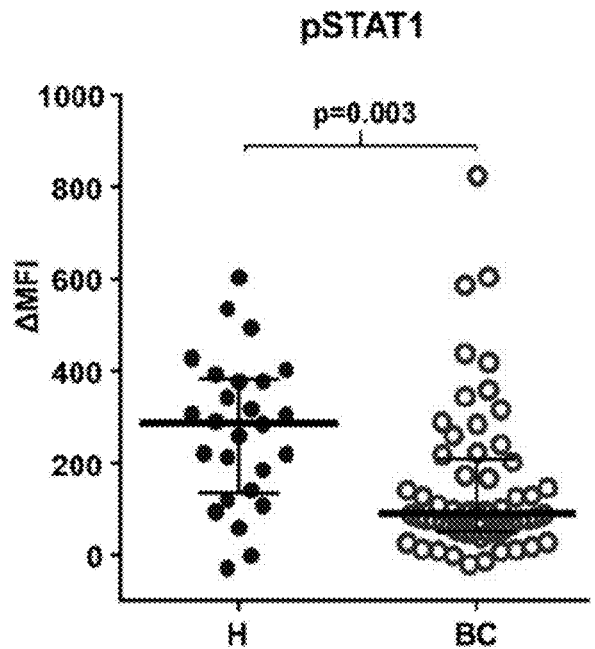
Figure 1C:
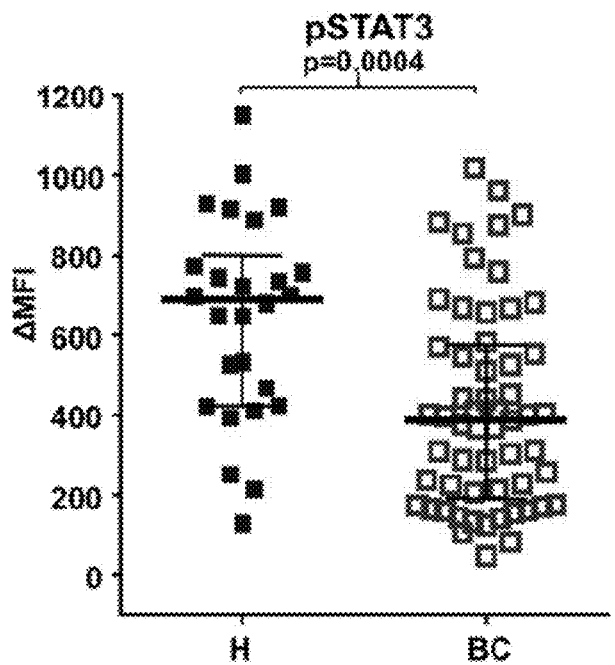
Figure 1D:
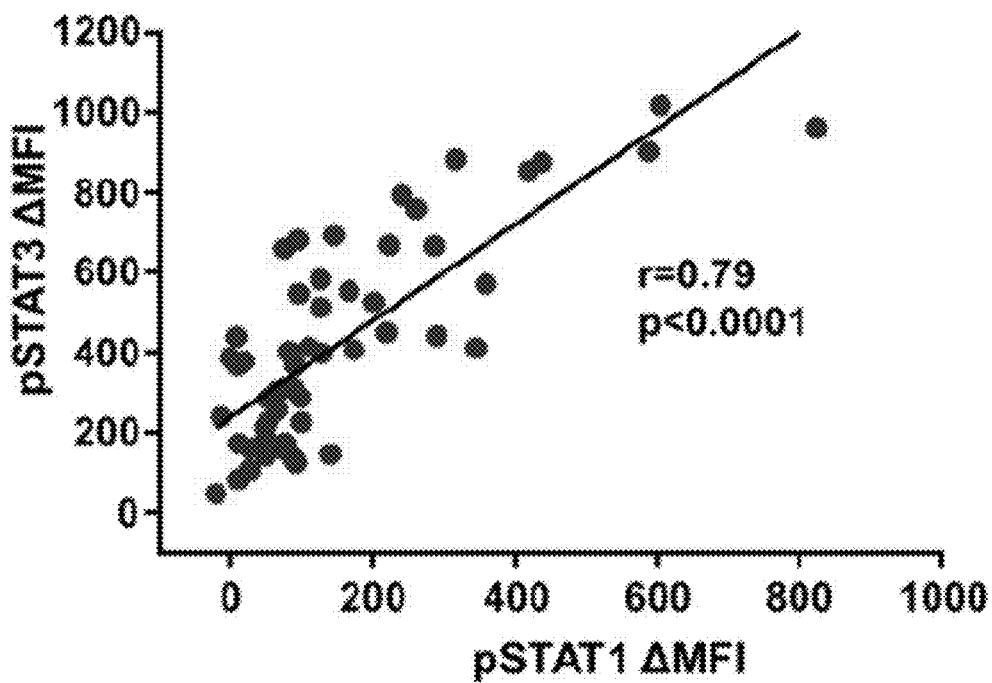

Defective IL-6 signaling responses in peripheral CD4+ T cells from breast cancer patients To investigate IL-6 immune biology in breast cancer patients, the inventors analyzed the responsiveness of peripheral blood immune cells to IL-6 in breast cancer patients and age-matched healthy donors. Clinical and pathological characteristics of the breast cancer patients are summarized in Table 1. Peripheral blood mononuclear cells (PBMCs) from breast cancer patients and healthy donors were stimulated with IL-6 and phosphorylation of STAT1 and STAT3 (pSTATs) were determined by phosphoflow cytometry (Critchley-Thorne et al, Proceedings of the National Academy of Sciences of the United States of America 2009; 106:9010-5). IL-6 signaling response (ΔMFI) was represented by IL-6 stimulated minus unstimulated pSTATs median fluorescence intensity (MFI) (FIG. 1A). The inventors examined IL-6 signaling response in T cells (CD3+), B cells (CD20+), NK cells (CD16+) and myeloid cells (CD33+) and found that IL-6 induced phosphorylation of STAT1 (p=0.003) and STAT3 (p=0.0004) in naïve CD4+ T cells from breast cancer patients (n=57) was significantly lower than that in healthy donors (n=26) (FIG. 1B, FIG. 1C). To determine whether the observed lower IL-6 signaling response was due to reduced total available STATs, the inventors compared the levels of total STAT1 and STAT3 in naïve CD4+ T cells by flow cytometry and found similar levels of total STAT1 and STAT3 between breast cancer patients and healthy donors. In addition, the inventors found similar levels of basal pSTAT1 and pSTAT3 in naïve CD4+ T cells between breast cancer patients and healthy donors (data not shown). In cancer cells, STAT1 and STAT3 are considered to play opposing roles in tumorigenesis where STAT3 is tumor-promoting and STAT1 is tumor-inhibiting (Avalle et al, JAKSTAT 2012; 1:65-72; Salgado et al, Int J Cancer 2003; 103:642-6). In contrast, the inventors found that IL-6 induced phosphorylation of STAT1 and STAT3 were highly correlated in T cells (FIG. 1D), indicating that the IL-6-STAT pathway is coordinately dysfunctional in breast cancer patients.

TABLE 1

Patient Characteristics

| Characteristics | Patients (N = 57) |
|---|---|
| Age - year | |
| Median | 51 |
| Range | 27-85 |
| Tumor stage - No. (%) | |
| DCIS | 7 (12.3) |
| T1 | 23 (40.4) |
| T2 | 15 (26.3) |
| T3 | 8 (14.0) |
| Unknown | 4 (7.0) |
| Grade - no. (%) | |
| G1 | 7 (12.3) |
| G2 | 22 (38.6) |
| G3 | 28 (49.1) |

TABLE 1-continued

Patient Characteristics

| Characteristics | Patients (N = 57) |
|---|---|
| Nodal Status - no. (%) | |
| N0 | 29 (50.9) |
| N1-3 | 24 (42.1) |
| Unknown | 4 (7.0) |
| Subtype - no. (%) | |
| Luminal | 45 (79.0) |
| HER2 | 6 (10.5) |
| Triple Negative | 6 (10.5) |

Figure 2A:
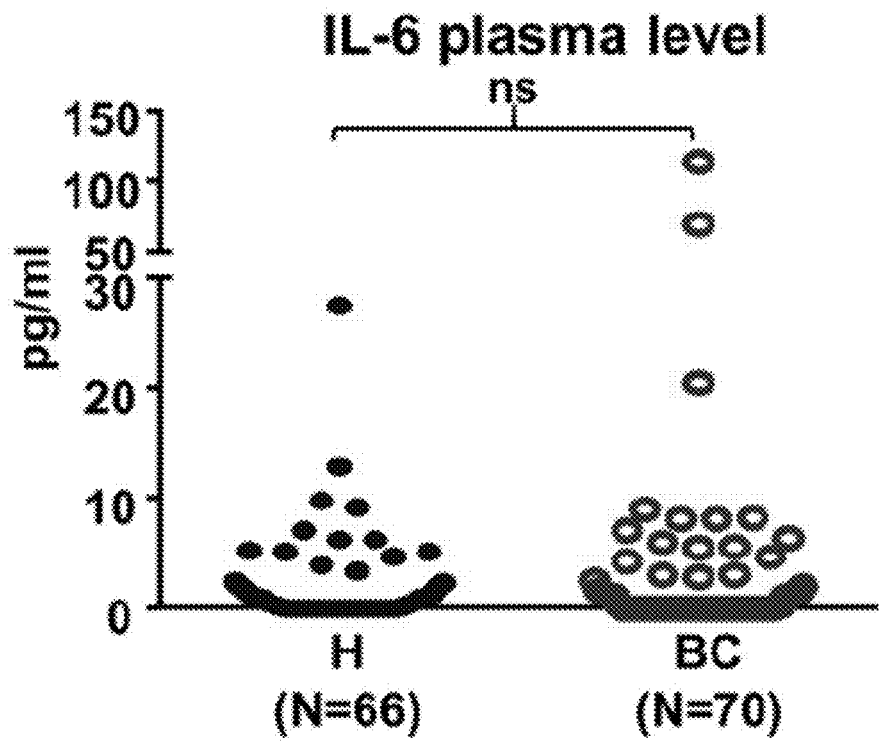
FIGS. 2A-2F show that impaired IL-6 signaling responses in naïve CD4+ T cells are not correlated with IL-6 plasma levels. H=healthy donor. BC=breast cancer patient.
Figure 2B:
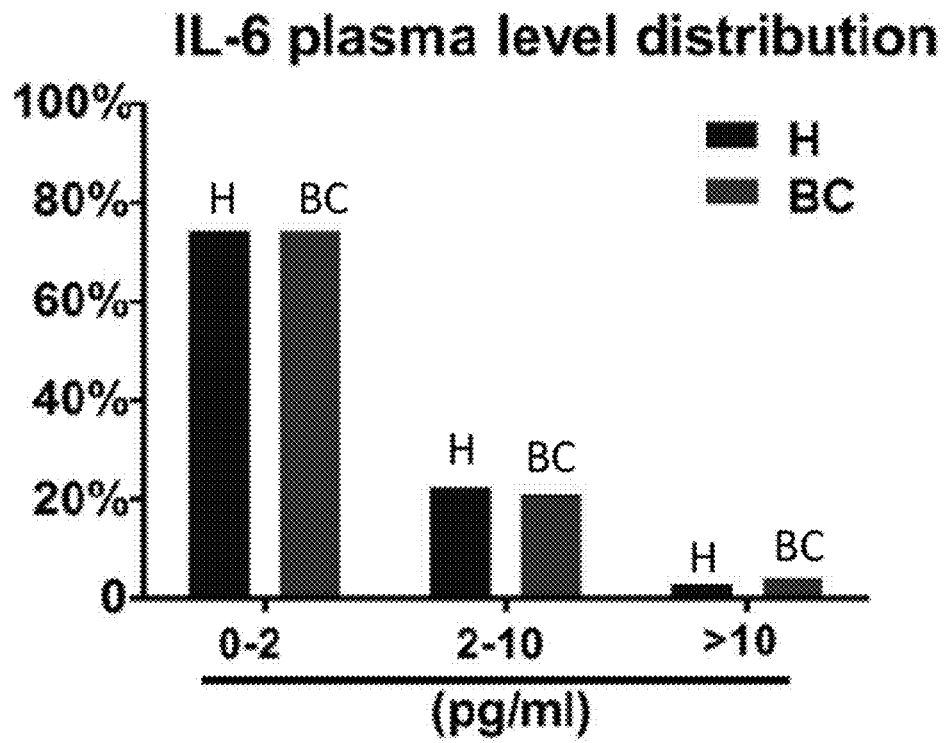
Figure 2C:
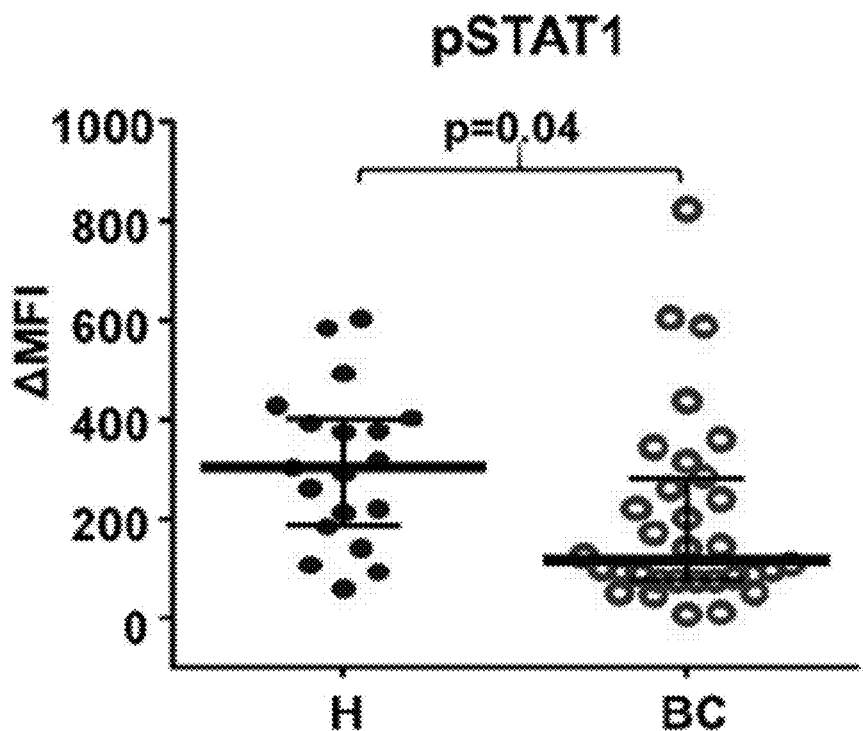
Figure 2D:
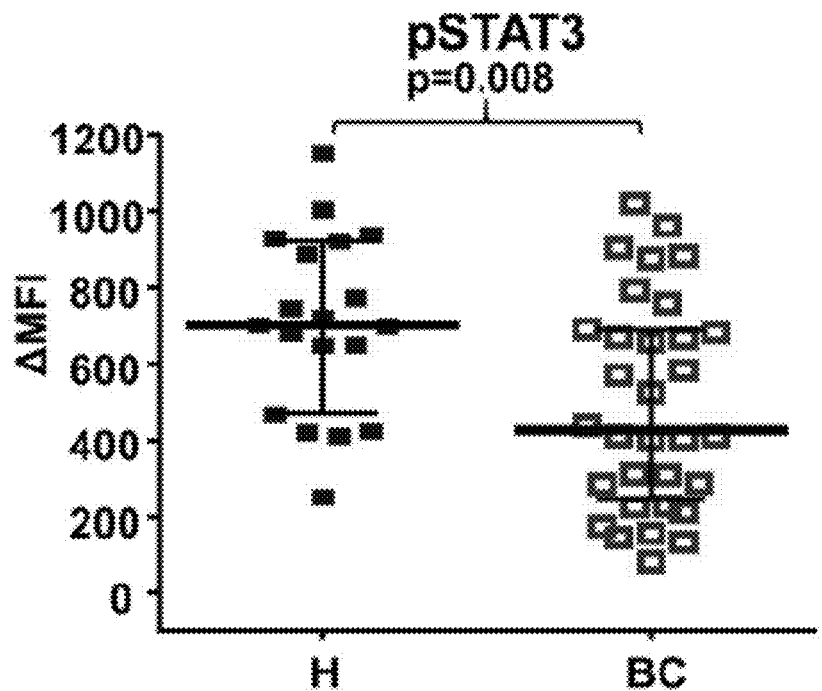
Figure 2E:
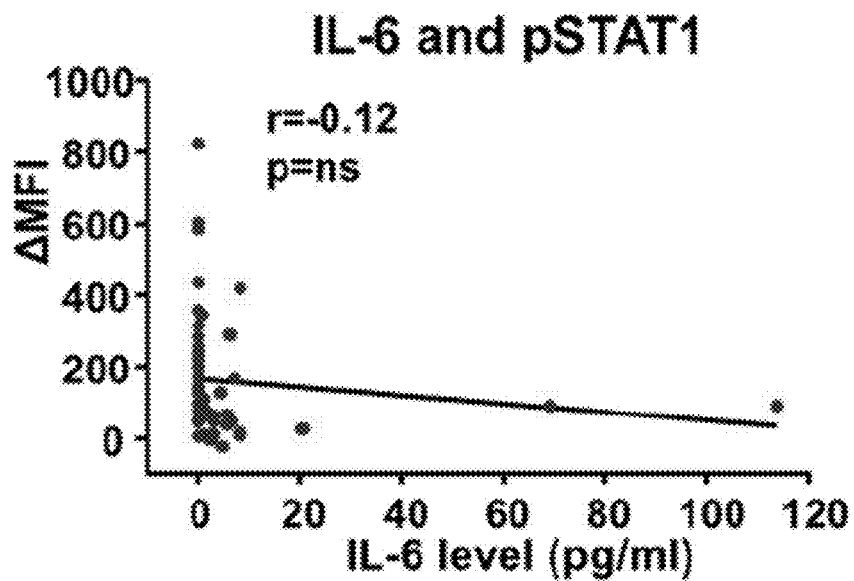
Figure 2F:
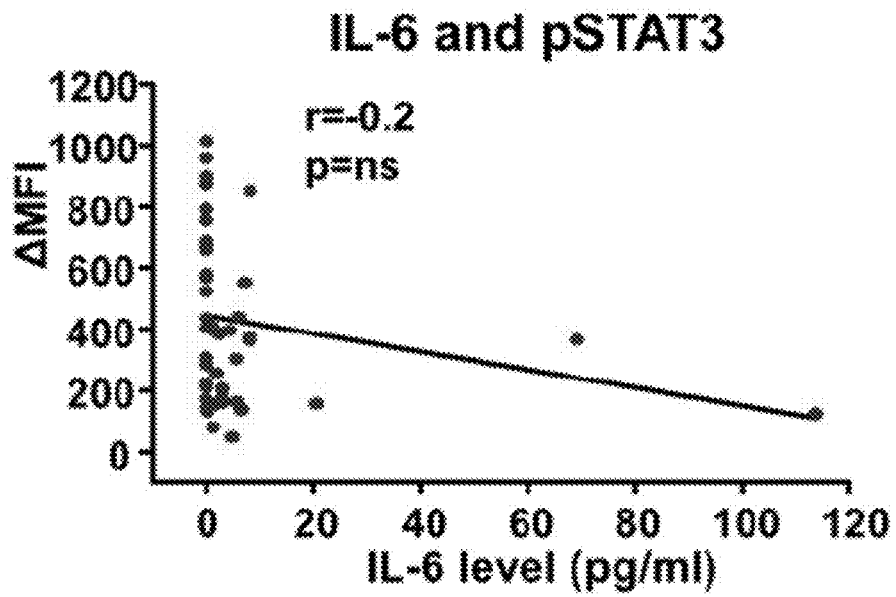

Elevated circulating IL-6 levels have been observed in advanced metastatic breast cancer patients which negatively correlate with patient outcome (Salgado et al, Int J Cancer 2003; 103:642-6; Bachelot et al, Br J Cancer 2003; 88:1721-6). To investigate whether impaired IL-6 signaling responses observed in breast cancer naïve CD4+ T cells were related to soluble IL-6 levels, the inventors compared plasma IL-6 levels between breast cancer patients (n=70) and age-matched healthy donors (n=66) by ELISA. All plasma samples from breast cancer patients were collected at diagnosis prior to surgery or any therapy. Interestingly, the inventors found that plasma IL-6 levels were not significantly elevated in this cohort of breast cancer patients (mean 4.2 pg/ml, median 0 pg/ml) as compared to healthy donors (mean 2.0 pg/ml, median 0.25 pg/ml) (FIG. 2A). As normal plasma IL-6 levels are generally in the range of 0-2 pg/ml (Ridker et al, Circulation 2000; 101:1767-72), the inventors further categorized patients' plasma IL-6 levels into three ranges (0-2 pg/ml, 2-10 pg/ml, >10 pg/ml) and found similar distributions between breast cancer patients and healthy donors (FIG. 2B). Importantly, the inventors compared the IL-6 signaling responses in T cells between healthy donors and breast cancer patients who had normal IL-6 plasma levels (0-2 pg/ml) at diagnosis. IL-6 induced phosphorylation of STAT1 (p=0.04) and STAT3 (p=0.008) in naïve CD4+ T cells from breast cancer patients was still significantly lower than that in healthy donors even though they all had plasma IL-6 levels in the normal range (FIG. 2C, FIG. 2D). Moreover, the inventors found no significant correlation between plasma IL-6 levels and IL-6 induced pSTATs in T cells (FIG. 2E, FIG. 2F).

Figure 3A:
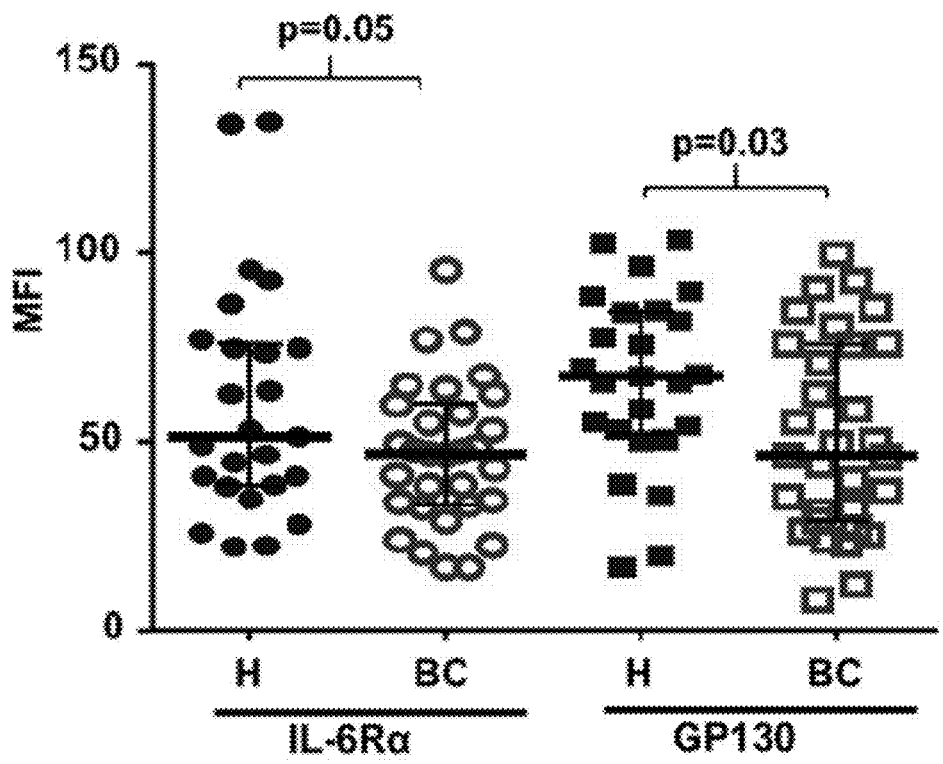
FIGS. 3A-3H show that impaired IL-6 signaling responses in naïve CD4+ T cells is associated with lower IL-6 receptor levels and defective Th17 differentiation. H=healthy donor. BC=breast cancer patient In FIG. 3A, surface expression levels of IL-6Rα (p=0.05) and gp130 (p=0.03) on naïve CD4+ T cells from healthy donors (n=25) and breast cancer patients (n=31) were determined by flow cytometry with anti-IL-6Rα and anti-gp130 antibodies.
Figure 3B:
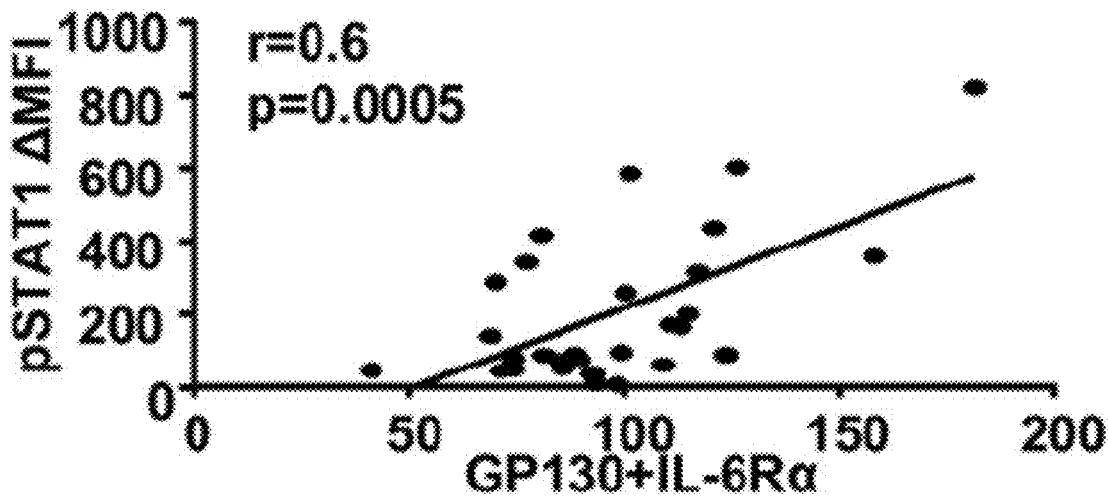
Figure 3C:
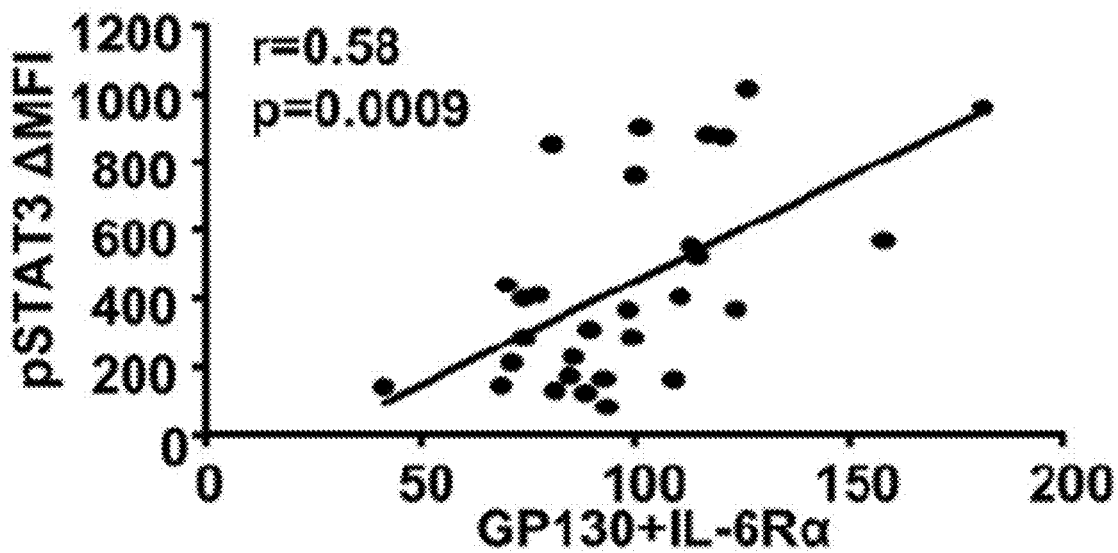
Figure 3D:
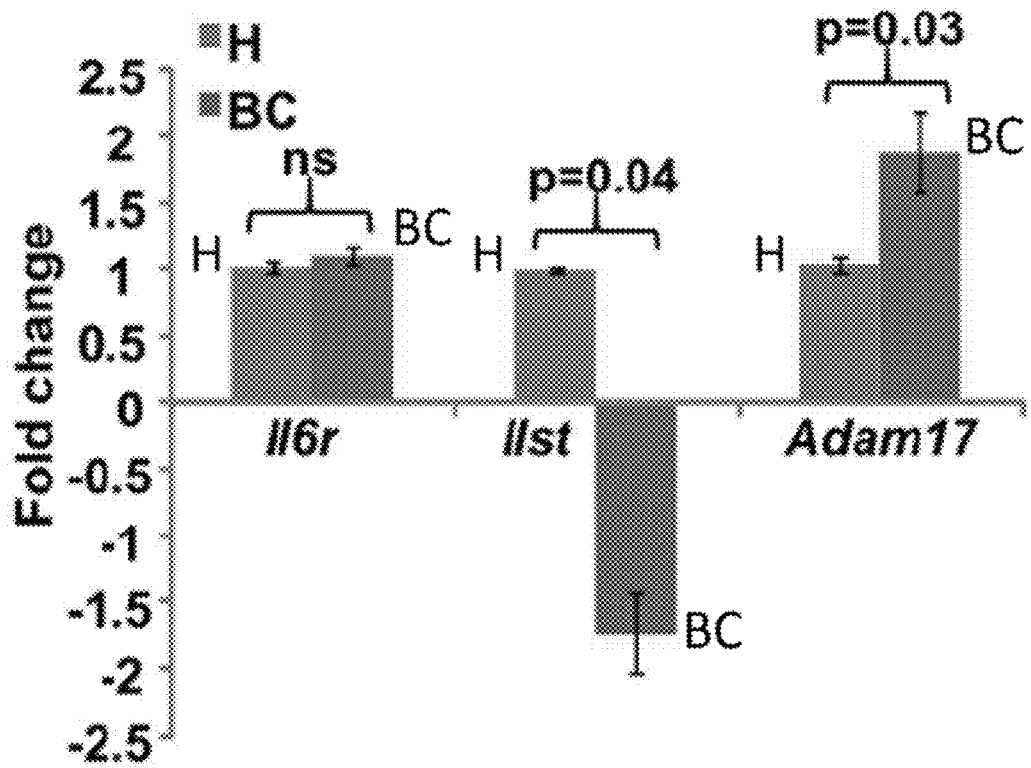

To investigate whether the impaired IL-6 signaling response was caused by reduced levels of the IL-6 receptor complex, the inventors compared the cell surface levels of IL-6Rα and gp130 in naïve CD4+ T cells between breast cancer patients and healthy donors by flow cytometry. Indeed, the inventors found that IL-6Rα (p=0.05) and gp130 (p=0.03) levels were both lower in breast cancer patients than in healthy donors (FIG. 3A). In addition, IL-6 induced pSTATs significantly correlate with the level of IL-6Rα plus gp130 (pSTAT1: p=0.0005; pSTAT3: p=0.0009) (FIG. 3B, FIG. 3C). To address whether these changes were regulated at the transcriptional level, the inventors measured the mRNA levels of IL-6Rα and gp130 in CD4+ naïve T cells by qPCR. Indeed, mRNA levels of gp130 (Il6st) (p=0.04) were significantly lower in T cells from breast cancer patients (n=4) than in healthy donors (n=4), but not IL-6Rα (Il6r) (FIG. 3D). IL-6Rα on the cell surface is known to be subjected to proteolytic cleavage by a metallopeptidase ADAM 17 (Schumacher et al, J Biol Chem 2015; 290: 26059-71). Surprisingly, the inventors found that mRNA levels of ADAM17 were significantly higher (p=0.03) in T cells from breast cancer patients than healthy donors (FIG.

3D). These data indicate that impaired IL-6 signaling responses in T cells from breast cancer patients are caused by reductions in both chains of the IL-6 receptor complex via two distinct mechanisms: gp130 via reduced transcription, and IL-6Rα via enhanced cleavage by ADAM17.

Figure 3E:
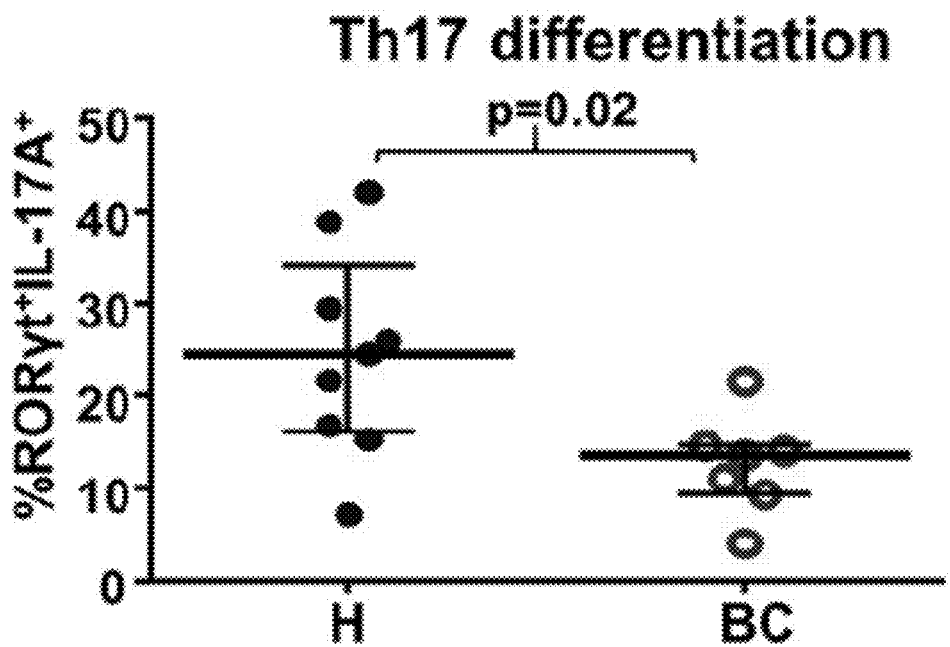
Figure 3F:
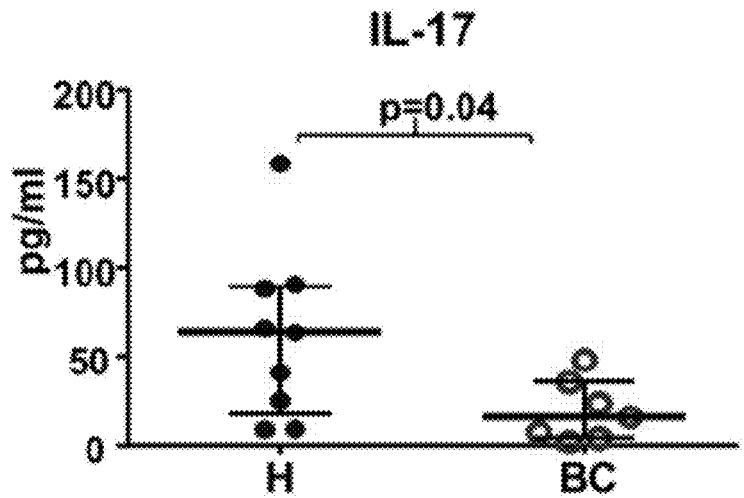
Figure 3G:
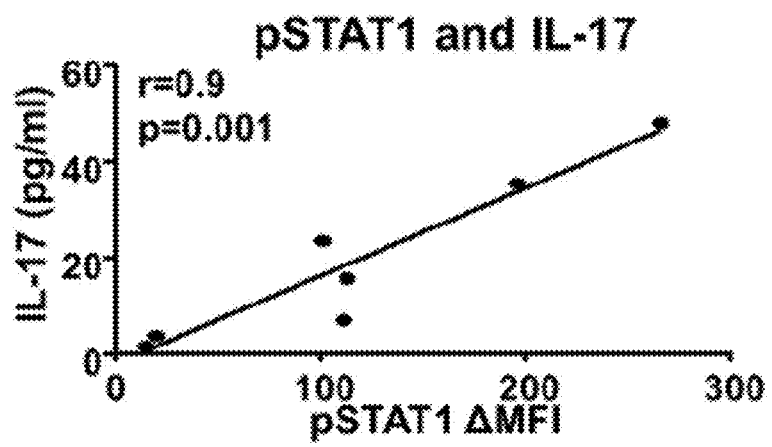
Figure 3H:
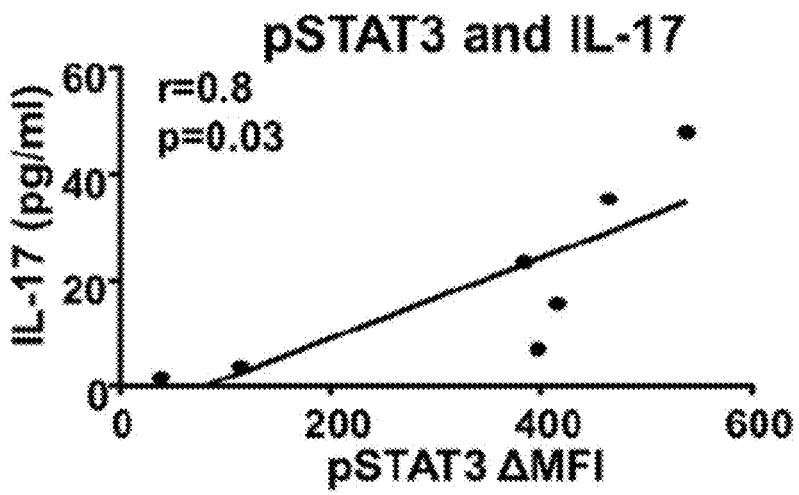

Since IL-6 is critical for Th17 differentiation (Kimura et al, European journal of immunology 2010; 40:1830-5), the inventors examined whether dysfunctional IL-6 signaling responses in naïve T cells from breast cancer patients was associated with impaired Th17 differentiation. Naïve CD4$^+$ T cells were isolated from fresh PBMCs and cultured in Th17 differentiation medium for 7 days. Breast cancer patient samples (n=7) exhibited fewer differentiated Th17 cells (RORγt$^+$ IL-17A$^+$) (p=0.02) (FIG. 3E) with lower IL-17 secretion levels (p=0.04) (FIG. 3F) than age-matched healthy donors (n=9). Among the breast cancer patients, IL-6 induced pSTATs significantly correlated with levels of IL-17 production (pSTAT1: p=0.001; pSTAT3: p=0.03) (FIG. 3G, FIG. 3H).

IL-6 signaling responses in peripheral CD4$^+$ T cells as prognostic marker

Figure 4A:
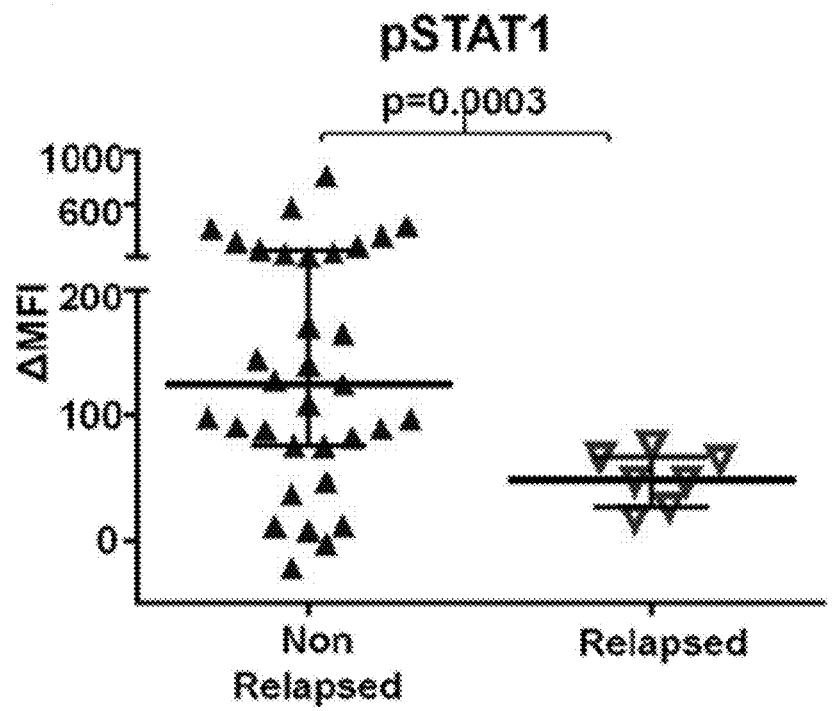
FIGS. 4A-4D show that IL-6 signaling response in peripheral blood CD4+ naïve T cells at diagnosis is correlated with clinical outcome.
Figure 4B:
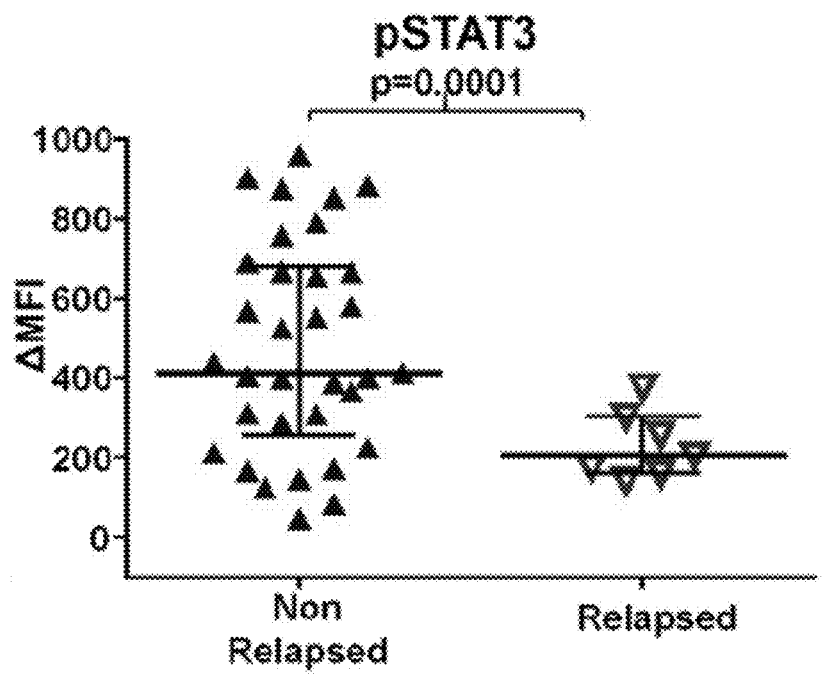
Figure 4C:
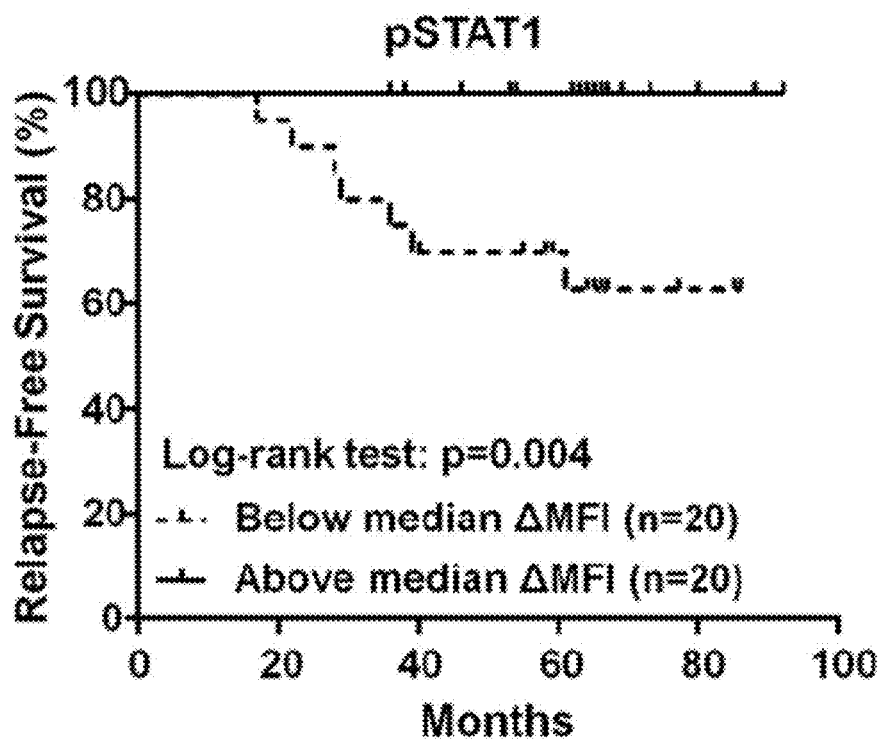
Figure 4D:
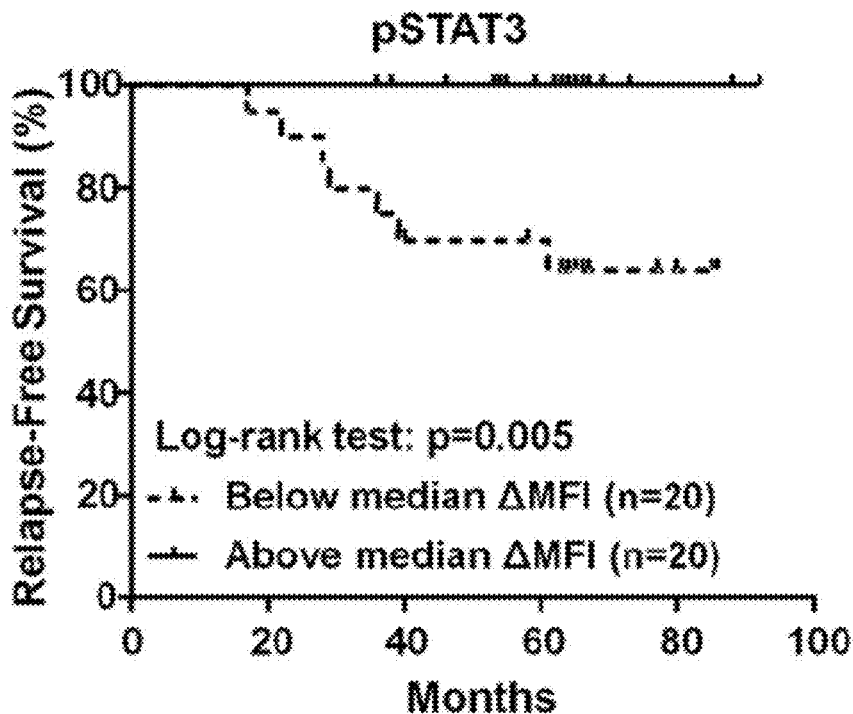

To evaluate the clinical significance of IL-6 signaling responsiveness, the inventors compared the IL-6 induced pSTATs responses in peripheral naïve CD4$^+$ T cells between relapsed and non-relapsed breast cancer patients. Only patients with blood collected at diagnosis prior to surgery or any therapy who had been clinically followed for at least 36 months were selected for this analysis. The median follow-up time of breast cancer patients (n=40) was 63 months (range 17-92 months). The inventors found that IL-6 induced phosphorylation of STAT1 (p=0.0003) and STAT3 (p=0.0001) in peripheral blood naïve T cells at diagnosis were significantly lower in patients who went on to relapse than those who remained disease-free (FIG. 4A, FIG. 4B). Kaplan-Meier survival analysis was performed to determine the relationship between IL-6 signaling responses and relapse-free survival. To divide breast cancer patients (n=40) into two populations in an unbiased way, median ΔMFI of IL-6 induced pSTAT1 or pSTAT3 was used as the cut-off Breast cancer patients with pSTAT1 (p=0.004) or pSTAT3 (p=0.005) ΔMFI below the median (n=20) had significantly worse relapse-free survival than those above the median ΔMFI (n=20) (FIG. 4C, FIG. 4D), indicating that lower IL-6 signaling responses predict worse relapse-free survival. Intriguingly, none of the patients with IL-6 signaling responses above the median experienced relapse over 100 months (FIG. 4C, FIG. 4D).

To understand if the IL-6 signaling response changes over time amongst relapsed breast cancer patients, the inventors compared the IL-6 signaling response between patients with blood collected at diagnosis (n=7) and patients with blood collected at the time of relapse (n=7). The inventors found no significant difference in IL-6 induced pSTAT levels (data not shown), indicating that impaired IL-6 signaling in T cells is a persistent defect that develops early in some patients, prior to diagnosis, who are at higher risk for relapse. In a multivariate analysis adjusted for age, tumor stage, grade, nodal status and subtype of breast cancer patients, IL-6 induced phosphorylation of STAT1 (p=0.001) or STAT3 (p=0.005) still retained the prognostic significance for relapse-free survival, indicating that IL-6 signaling responses could be a predictor of clinical outcome independent of these clinicopathologic characteristics (Table 2). The associations between IL-6 signaling response in T cells and clinicopathologic characteristics of breast cancer patients was also evaluated and no significant correlations were found between IL-6 signaling responses and age, tumor stage, grade, T status or subtype (data not shown). Therefore, these findings show that IL-6 signaling responsiveness in peripheral naïve CD4$^+$ T cells could be developed into a prognostic blood test to predict the clinical outcome of breast cancer patients.

TABLE 2

Univariate and multivariate analysis for relapse-free survival by Cox regression.

| Variables | Univariate p-value | Multivariate p-value |
|---|---|---|
| pSTAT1 | 0.006 | 0.001 |
| pSTAT3 | 0.015 | 0.005 |

The multivariate p-value is adjusted for age, tumor stage, grade, nodal status, and subtype.

Each of the references, journal articles, patents, publications, and books cited herein are incorporated by reference herein in their entirety.

What is claimed is:

1. A method of predicting an increased probability of breast cancer relapse in a breast cancer patient in need thereof, the method comprising:
   (i) obtaining a peripheral blood sample comprising T cells from the patient;
   (ii) contacting the peripheral blood sample with either:
      (a) an IL-6 pathway detection agent capable of binding an IL-6 pathway protein, wherein the IL-6 pathway protein is phosphorylated STAT1, phosphorylated STAT3, IL-6Rα, or ADAM17, thereby forming a detectable complex; or
      (b) an IL-6 pathway probe capable of hybridizing an IL-6 pathway mRNA expression sequence, wherein the IL-6 pathway mRNA expression sequence is gp130, thereby forming a hybridization complex;
   (iii) detecting and/or quantifying: (a) the detectable complex, or (b) the hybridization complex, respectively;
   (iv) predicting an increased probability of breast cancer relapse in the breast cancer patient when:
      (1) the T cells from the breast cancer patient are less responsive to IL-6 relative to a standard control;
      (2) the breast cancer patient has a lower level of IL-6Rα relative to a standard control;
      (3) the breast cancer patient has a higher level of ADAM17 relative to a standard control; or
      (4) the breast cancer patient has a lower level of gp130 relative to a standard control; and
   (v) administering to the breast cancer patient having an increased probability of breast cancer relapse an effective amount of an anti-cancer agent.

2. The method of claim 1, further comprising monitoring the patient for breast cancer relapse.

3. The method of claim 1, wherein the anti-cancer agent is hormone replacement therapy, a chemotherapeutic agent, radiation therapy, or a combination of two or more thereof.

4. The method of claim 1, further comprising monitoring the patient for breast cancer relapse and administering to the patient an anti-cancer agent.

5. The method of claim 1, further comprising classifying the patient as having increased risk for relapse when the patient has a different IL-6 activity relative to a standard control.

6. The method of claim 1, further comprising classifying the patient as having decreased risk for relapse when the patient has a similar IL-6 activity relative to a standard control.

7. The method of claim 1, wherein the T cells are CD4+ T cells.

8. The method of claim 7, wherein the CD4+ T cells are naïve CD4+ T cells.

9. A method of treating breast cancer in a patient having an increased risk for breast cancer relapse, the method comprising:
   (i) determining IL-6 activity in the patient, and identifying the patient as having an increased risk for breast cancer relapse when:
      (a) the T cells from the patient are less responsive to IL-6 relative to a standard control;
      (b) the patient has a lower level of IL-6Rα relative to a standard control;
      (c) the patient has a higher level of ADAM17 relative to a standard control; or
      (d) the patient has a lower level of gp130 relative to a standard control; and
   (ii) administering to the patient an effective amount of an anti-cancer agent.

10. The method of claim 9, further comprising monitoring the patient for breast cancer relapse.

11. The method of claim 9, wherein determining the IL-6 activity in the patient comprises:
   (i) obtaining a peripheral blood sample comprising T cells from the patient;
   (ii) contacting the peripheral blood sample with either:
      (a) an IL-6 pathway detection agent capable of binding an IL-6 pathway protein, wherein the IL-6 pathway protein is phosphorylated STAT1, phosphorylated STAT3, IL-6Rα, or ADAM17; thereby forming a detectable complex; or
      (b) an IL-6 pathway probe capable of hybridizing an IL-6 pathway mRNA expression sequence, wherein the IL-6 pathway mRNA expression sequence is gp130; thereby forming a hybridization complex;
   (iii) detecting and/or quantifying: (a) the detectable complex, or (b) the hybridization complex, respectively.

12. The method of claim 9, wherein the anti-cancer agent comprises hormone replacement therapy, a chemotherapeutic agent, radiation therapy, or a combination of two or more thereof.

* * * * *

UNITED STATES PATENT AND TRADEMARK OFFICE
CERTIFICATE OF CORRECTION

PATENT NO. : 11,187,704 B2
APPLICATION NO. : 16/660524
DATED : November 30, 2021
INVENTOR(S) : Peter P. Lee Page 1 of 1

It is certified that error appears in the above-identified patent and that said Letters Patent is hereby corrected as shown below:

In the Specification

Delete the paragraph at Column 1, Lines 17-22, in its entirety and insert the following:
--This invention was made with government support under W81XWH-10-1-0616 and W81XWH-06-1-0417 awarded by the Defense Health Agency, Medical Research and Development Branch, and AI007290 and R01 CA130817 awarded by the National Institutes of Health. The government has certain rights in the invention.--

Signed and Sealed this
Eighteenth Day of March, 2025

Coke Morgan Stewart
*Acting Director of the United States Patent and Trademark Office*

SEQUENCE LISTING

```
<160> NUMBER OF SEQ ID NOS: 6

<210> SEQ ID NO 1
<211> LENGTH: 20
<212> TYPE: DNA
<213> ORGANISM: Artificial sequence
<220> FEATURE:
<223> OTHER INFORMATION: Synthetic polynucleotide

<400> SEQUENCE: 1
ttgtttgtga gtggggtcct                                          20

<210> SEQ ID NO 2
<211> LENGTH: 20
<212> TYPE: DNA
<213> ORGANISM: Artificial sequence
<220> FEATURE:
<223> OTHER INFORMATION: Synthetic polynucleotide

<400> SEQUENCE: 2
```

```
tgggactcct gggaatactg                                                    20

<210> SEQ ID NO 3
<211> LENGTH: 20
<212> TYPE: DNA
<213> ORGANISM: Artificial sequence
<220> FEATURE:
<223> OTHER INFORMATION: Synthetic polynucleotide

<400> SEQUENCE: 3
aggaccaaag atgcctcaac                                                    20

<210> SEQ ID NO 4
<211> LENGTH: 20
<212> TYPE: DNA
<213> ORGANISM: Artificial sequence
<220> FEATURE:
<223> OTHER INFORMATION: Synthetic polynucleotide

<400> SEQUENCE: 4
gaatgaagat cgggtggatg                                                    20

<210> SEQ ID NO 5
<211> LENGTH: 24
<212> TYPE: DNA
<213> ORGANISM: Artificial sequence
<220> FEATURE:
<223> OTHER INFORMATION: Synthetic polynucleotide

<400> SEQUENCE: 5
actctgagga cagttaacca aacc                                               24

<210> SEQ ID NO 6
<211> LENGTH: 24
<212> TYPE: DNA
<213> ORGANISM: Artificial sequence
<220> FEATURE:
<223> OTHER INFORMATION: Synthetic polynucleotide

<400> SEQUENCE: 6
agtaaaagga gccaatacca caag                                               24
```